(12) United States Patent
Cimo

(10) Patent No.: US 12,251,595 B1
(45) Date of Patent: *Mar. 18, 2025

(54) MUSCLE MEMORY TRAINING APPARTUS AND METHOD OF USE

(71) Applicant: Gaetano Cimo, Laguna Niquel, CA (US)

(72) Inventor: Gaetano Cimo, Laguna Niquel, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/601,881

(22) Filed: Mar. 11, 2024

Related U.S. Application Data

(63) Continuation-in-part of application No. 18/233,317, filed on Aug. 12, 2023, now Pat. No. 11,925,593.

(51) Int. Cl.
| | |
|---|---|
| *A61H 23/00* | (2006.01) |
| *A61B 5/11* | (2006.01) |
| *A63B 21/22* | (2006.01) |
| *A61H 23/02* | (2006.01) |

(52) U.S. Cl.
CPC ............ *A63B 21/22* (2013.01); *A61B 5/1101* (2013.01); *A61B 2505/09* (2013.01); *A61H 23/0263* (2013.01); *A61H 2023/0281* (2013.01); *A61H 2203/0406* (2013.01)

(58) Field of Classification Search
CPC ... A61B 5/1101; A61B 2505/09; A63B 21/22; A61H 23/0263; A61H 2203/0406; A61H 2023/0281
See application file for complete search history.

(56) References Cited

U.S. PATENT DOCUMENTS

| | | | |
|---|---|---|---|
| 3,951,260 A | 4/1976 | Frazee | |
| 4,809,896 A | 3/1989 | McColly | |
| 5,261,394 A | 11/1993 | Mulligan et al. | |
| 9,408,774 B2 | 8/2016 | Rafaeli | |
| 10,507,155 B1* | 12/2019 | Cimo | ...................... A61H 23/00 |
| 2003/0006357 A1* | 1/2003 | Kaiser | ................... F16F 7/1005 |
| | | | 248/550 |
| 2012/0253247 A1* | 10/2012 | Aoki | ................... A63B 21/4043 |
| | | | 601/112 |
| 2013/0018283 A1* | 1/2013 | Halkias | ................ A61B 5/1101 |
| | | | 600/595 |

(Continued)

*Primary Examiner* — Timothy A Stanis

(57) ABSTRACT

A muscle memory training apparatus mitigates movement disorders by restoring muscle memories, aka motor learning, that have become aberrant. It restores reflex stabilization muscle memories thereby providing a stable platform upon which voluntary muscle memories are restored. It is based on the universally accepted fact that muscle memories may be improved with practice and the yet to be accepted fact that reflexes execute muscle memories that may likewise be improved. The muscle memory training apparatus is attached to the user and generates centrifugal forces of adjustable amplitude, frequency, duration, and direction, to emulate forces, perturbations, stabilization systems are designed to countervail. Each perturbation, applied several times per second, effectuates reflex muscle memories that contract muscles that countervail the perturbations. Reflex muscle memories and voluntary muscle memories are practiced concurrently as they interact with each other and are integral to the biological movement system.

20 Claims, 20 Drawing Sheets

(56) References Cited

U.S. PATENT DOCUMENTS

| | | | |
|---|---|---|---|
| 2014/0180184 A1* | 6/2014 | Duguid | A61H 3/00 601/87 |
| 2014/0260714 A1* | 9/2014 | Vallery | G01C 19/04 74/5.37 |
| 2015/0209212 A1* | 7/2015 | Duguid | A61H 3/00 601/87 |
| 2023/0301864 A1* | 9/2023 | Barwick | A61H 3/00 |

* cited by examiner

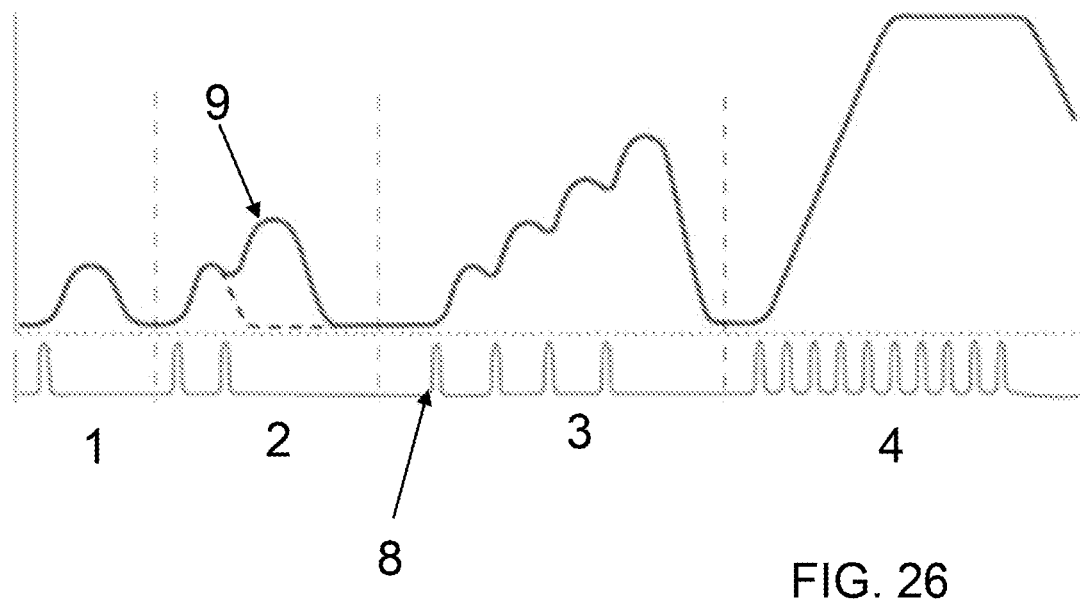
FIG. 26
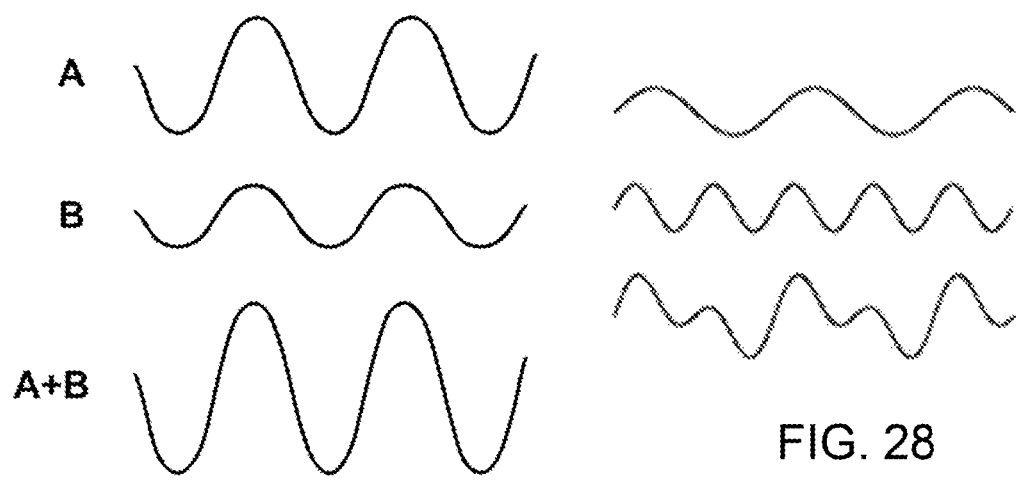
FIG. 28
FIG. 27

MUSCLE MEMORY TRAINING APPARTUS AND METHOD OF USE

CROSS REFERENCE TO RELATED APPLICATIONS

This application claims the benefit of priority to U.S. patent application Ser. No. 18/233,317, filed on Aug. 12, 2023, and currently pending; the entirety of which is hereby incorporated by reference herein.

BACKGROUND OF THE INVENTION

Field of the Invention

The invention relates to systems, devices, and methods for mitigating movement disorders, and more specifically relates to restoration of aberrant stabilization reflex and voluntary muscle memories with practice.

Background

Drugs

Drug treatment is the best-known therapy for mitigation of movement disorders. However, in addition to disastrous side effects and possible drug dependency issues, they can cause movement disorders. Levodopa and dopamine agonists are known to cause proprioception deficits and drug induced dyskinesia. A drug taken to mitigate some symptoms is likely to exasperate other symptoms. Treatment for tremor may cause balance defects. In fact, drugs taken to mitigate movement disorders affect other organism regulatory systems. For example, the same drug used to suppress tremor is used to limit blood pressure. One cannot treat one without inadvertently treating the other. The unintended consequences are called side effects.

Deep Brain Stimulation [DBS]

DBS requires a pacemaker type device to be surgically implanted in the brain. Experts are unclear how DBS works, but by sending high frequency electrical impulses into specific areas of the brain it can mitigate symptoms. DBS is regarded as a last resort means of mitigating movement disorders.

Devices for Tremor

Tremor mitigation devices are attached or worn. Some dampen tremors with gyroscopes or utilize viscous liquids, elastic materials, and magnetic fields. Such devices may attenuate tremor; however, they inadvertently dampen voluntary movement as well. Tremor cancellation devices apply a countervailing force that cancels the tremor. Such devices include exoskeletons that are worn over the arm or hand. They are affixed with active mechanisms that sense tremor motion and produce countervailing forces. Such devices may be uncomfortable, expensive and suppress intentional motion. Tremor Isolation devices isolate the tremor from a stabilized object. The subject grasps a platform that is loosely coupled to the object platform. As the object attempts to follow the tremor motion, its motion is sensed and converted to electrical output that drives actuators attached to the object platform with opposing forces thereby preventing the object from moving. Such systems do not attempt to suppress tremors but allow them to be insulated from an object. Buildings are isolated from earthquakes, weapon systems from vibrating platforms and handheld devices isolate a person's tremor from a utensil, spoon, scalpel, or paint brush. Such devices are only effective while being worn and activated. There is little or no persistent, long-term effect, following their use.

Devices for Balance

Wearable devices are used to mitigate balance or gait disorders. They are attached to a person's body close to the center of mass. Some use variable-speed control moment gyroscopes (VSCMGs). The VSCMGs generate offsetting forces that counteract a fall to any direction. Such devices are alternative balancing systems that supplement or bypass the biological balance system. To prevent dependency and maladaptation of the biological stabilization system on such devices, they should only assist as needed to provide only the support that is necessary to fulfill a task, such as recovering balance during a falling event.

Other systems do not provide counteracting forces. They sense and communicate early warning signals i.e. vibration, to the user indicating the user is starting to or is falling in a particular direction. The user may "actively compensate"; use voluntary movement, to countervail imbalances. They use voluntary movement to do the job that reflexes are designed to do.

Some devices randomly perturb a user's balance that a user anticipates and prepares for by tensing muscles and assuming defensive postures then responds to with voluntary movements intended to countervail the perturbations. They also "actively compensate"; use voluntary movement, to do the job that reflexes are designed and designated to do.

Rehabilitation Therapy

People automatically rehabilitate by adopting compensatory measures. For example, irregular posture and movement is assumed to avoid falling. People crouch or lean forward, outstretch hands, position feet apart, and avoid unnecessary movement to keep their center of gravity low and over a large base of support. They deploy defensive movements like moving slowly, avoiding sharp turns, and walking backwards. They shuffle their feet while walking so that both feet are always in contact with the floor. Freezing reduces the risk of falling.

Other measures include behavioral changes like avoidance of difficult motor tasks and movements, like standing, walking, or threading a needle. The use of assistive devices like walkers, crutches, wheelchairs, and care givers, are common ways of coping.

Prescribed therapies like physical therapy, Tai Chi, dancing, boxing, and practicing fine motor skills are evolved and optimized methods of rehabilitation. They train voluntary muscle memories to adapt to an unstable platform.

Compensatory Measures

Whether adapted automatically or as a prescribed treatment, drugs, assistive devices, and rehabilitation therapies are compensatory mechanisms that provide symptom relief and do not correct underlying causes of movement disorders. They are interventions that interfere with or modulate and thereby accelerate the deterioration of biological systems and processes. For example, active compensation, the use of voluntary movement to compensate for deficit automatic movement, diverts cognitive resources from thinking to control of movement normally handled by reflexes. When the brain becomes preoccupied with micromanaging functions normally delegated, cognitive demands must wait. That is why people with movement disorders appear to not being able to walk and talk at the same time. In another example, using a walker reduces demand on neurons, muscles, and muscle memories, causing them to atrophy. Paradoxically, the more effective the treatment, the more ineffective endogenous processes become. The aberrant movements become the new "norm". Such treatments may be the only recourse for some people; however, biological systems are capable of healing themselves!

Restoration Therapy

Some forms of rehabilitation restore reflex stabilization. For example, Romberg maneuvers and balance board training perturb balance that effectuates reflexes that can restore balance muscle memory.

The difference between current therapies and the invention that both use training of muscle memories to mitigate movement disorders, is which muscle memories are being trained, voluntary or reflexive. Current therapies train voluntary muscle memories to compensate for deficit reflex muscle memories. The invention trains reflex muscle memories that stabilize limb positions, balance, and muscle tension so that voluntary movement and muscle memories may perform upon a stabilized platform. The invention apparatus specifically trains reflex muscle memories that restore stabilization. Voluntary muscle memories are retrained concurrently to readapt from an unstable to stable platform.

Restoration is a Form of Self-Healing.

Plasticity makes restoration possible. It makes instantaneous to long-term changes in biological cells, organs, systems, and behaviors to protect, repair, and adapt processes to environmental conditions.

Neuroplasticity is the modification of the nervous system by changing the structure and thereby the functionality of individual neurons and their connectivity to other neurons and effectors. Muscle plasticity can make muscles bigger, stronger, and faster. Perhaps the most important feature of plasticity is that changes to individual components are made in concert with each other to achieve acceptable performance of systems. Movement is a system, from reflexes to motor skills to spontaneous voluntary movement, and it is plastic. Movement can be trained by practicing it. Movement is improved, restored, and performed with efficiency, accuracy, and automaticity. That is the natural way organisms are designed to be restored and plasticity produces long-term, persistent changes, restorations, and perhaps cures.

The invention provides the environmental conditions and challenges that effectuate plasticity to improve movement.

The Invention is Restoration Therapy.

Stabilization System

Reflexes are closed loop mechanisms that sense, respond to, and countervail unintentional movement. There are many manmade examples of such systems. For example, Battleship guns are mounted on stabilized platforms that isolate them from the movement of the ship. Whereas the ship may pitch, roll, yaw, and move in response to wind and shifting weights, the platform does not. Sensors detect the ship movement and actuators attached to the platform produce forces that countervail the ship movement.

In this manner, aiming the gun is greatly simplified as it is mounted on a stable rather than a moving platform. Similar technology is used with buildings that are stabilized against earthquakes and active suspension systems that stabilize an automobile against variations in road surface and reflexes that stabilize balance and joints against unintended movement.

Biological Stabilization Systems

Reflexes sense and execute muscle memories that countervail unintentional movement. When stabilization systems fail to do their job, or worse yet, cause rather than mitigate perturbations, intended movement is impaired. Aberrant reflex muscle memories cause voluntary muscle memories to become aberrant because they attempt to adapt to an unstable platform. Motor skills are extremely difficult to maintain when stabilization systems become deficit. A person with tremor, rigidity, imbalance, or inability to automatically sense and respond to unintended movement may practice a motor skill and never achieve adequate performance.

It is virtually impossible to develop or maintain motor skills on an unstable platform!

Voluntary Muscle Memory

Muscle memory is generally described as a voluntary movement that is essentially automatic and requires little or no cognitive intervention. Practicing movement with intent to improve and knowledge of performance increases accuracy, efficiency, and automaticity.

Reflex Muscle Memory

Reflex muscle memory can be improved the same way. But how do you cause a reflex to be effectuated? Unlike voluntary muscle memories that respond to conscious decision, reflex muscle memories respond to stimulus of sensory neurons. The apparatus stimulates sensory neurons the way they are designed to be stimulated. It delivers perturbations to stabilization reflexes. It stretches muscles effectuating stretch reflexes, perturbs balance effectuating balance reflexes and does so under varying load conditions that effectuate muscle tension reflexes. The perturbations and thereby the execution of the muscle memories is repeated over a protracted period and practiced multiple times per second. Practice improves the performance of the stabilization reflexes thereby restoring stabilization.

Stimulate Sensory Neurons the Way they are Designed to be Stimulated.

A System of Movements

Whether voluntary, reflexive, or imposed by external forces, movement causes multiple stabilization reflexes to be effectuated. For example, walking is voluntary, intentional movement, the execution of multiple voluntary muscle memories, that continuously change the center of gravity, the size and position of the base of support, and their relationship to each other, thereby perturbing balance and effectuating balance reflexes. Limbs are repositioned and that effectuates stretch reflexes. Shifting weight causes muscle tension reflexes. Walking would be countervailed, opposed, by reflexes, but for the system's ability to distinguish between forces caused by voluntary movement which are not to be countervailed and forces caused by perturbations to stabilization which are to be countervailed. Walking movements are not countervailed whilst the perturbations to stabilization caused by walking are.

In another example, a reflex causes movement that effectuates other reflexes. A person steps on a tack causing a withdrawal reflex, that contracts muscles lifting the foot to prevent further injury. That movement causes a shift in the body's center of gravity and a substantial shift in position and size of the base of support. But for other reflexes, the person would fall.

In another example, a person holds a barbell against their thighs while standing. The person extends their arms forward parallel to the floor and holds that position. The person changed the tension on several muscle groups including those in the back, shoulder, arms and hands, effectuating muscle tension reflexes, changed their center of gravity and its relationship with the base of support effectuating balance reflexes, and changed the intentional position of limbs effectuating stretch reflexes. The person assumed a new posture, and remains in balance, the barbell is not moving, and this change in posture is made without tension, balance and stretch reflexes countervailing the voluntary movement that got them there. Nor did the person lose stability during the voluntary movement. All the movement processes interact with each other, and all are integral to a plastic biological system that may be trained with practice and restored with practice when they become aberrant.

When perturbation is combined with voluntary movements like those of daily living activity or prescribed movements like exercises or practicing fine motor skills like writing or engaging in cognitive activity like carrying on a conversion, the entire movement system may be practiced.

It is the deficit system that must be restored and that is why it is the system that is should be practiced!

SUMMARY OF THE INVENTION

Purpose

The purpose of the invention is to mitigate movement disorders by restoring aberrant muscle memories which may be restored with practice. Reflex muscle memories are practiced by attaching an apparatus to the user that provides passive movement that repeatedly effectuates stabilization reflexes. Voluntary muscle memories that have maladapted to aberrant stabilization are practiced concurrently and readapted to an improving stabilized platform.

Reflex Restoration

The invention is directed to a muscle memory training apparatus that is attached to the user and generates perturbation forces of adjustable amplitude, frequency, duration, and direction to emulate forces, perturbations, stabilization systems are designed to countervail. Each perturbation, applied several times per second, effectuates reflex muscle memories that contract muscles that countervail the perturbations. Reflex muscle memories are practiced and thereby improved.

The apparatus consists of three assemblies, Perturbator that produces the perturbations, Motor Control that provides power, rotational direction, and rotational speed [RPM] to the Perturbator, and an Attachment that couples the perturbator to the user.

Perturbator

The perturbator is enclosed and houses a motor that rotates two weights in parallel orbits about a common motor axel. The weights are attached to arms that attach to the motor axel. The size of the weights, their position on the arms, and the motor rotational speed [RPM] are adjustable and control the amplitude and frequency of the perturbation forces. Arm and weight assemblies with fixed weights and positions are an alternative to the adjustable assemblies.

The perturbations may be generated in reverse order by reversing the rotation of the motor thereby changing the sequence in which reflexes are effectuated.

The two attachable arms may be orientated relative to the axel at the same angle wherein their centrifugal forces are in sync and produce no wobble, or at different angles like 180 degrees apart, wherein the centrifugal forces are out of phase thereby producing wobble the user feels as an alternating twisting force.

Attachment

The perturbator is coupled to a backpack worn by the user. The coupler allows the perturbator to set at different angles relative to the user thereby allowing the targeting of selective muscle groups. Note that perturbations caused by normal movement or environmental conditions are multi-directional as well.

Motor Control

In addition to controlling the motor speed and rotational direction as described, it may be programmed to dynamically modulate these parameters to fixed or random sequences.

Voluntary Movement Restoration

Performing daily routines or structured exercise routines whilst using the apparatus retrains voluntary muscle memories to perform in a stable environment.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 26 shows a graph of perturbing forces as a function of time.

FIG. 27 shows a graph of perturbing forces as a function of time.

FIG. 28 shows a graph of perturbing forces as a function of time.

Figure 1:
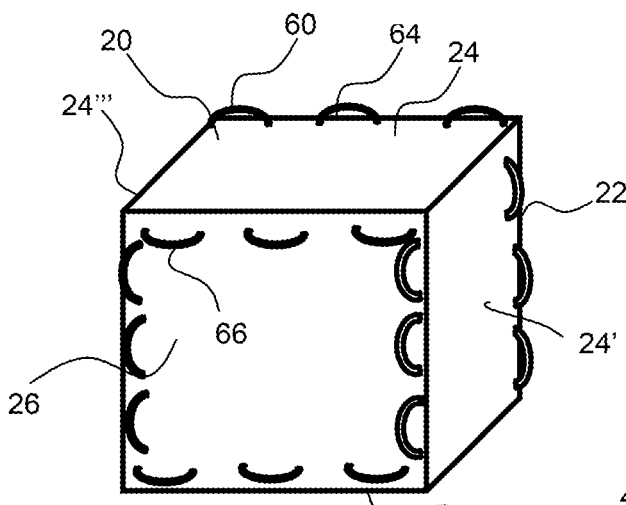
FIG. 1 shows an exemplary muscle memory training apparatus having a housing for the producing forces to off balance a person and a plurality retainers configured to retain a strap configured to extend from the muscle memory training apparatus to a person.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations, and improvements of the described embodiments, will occur to those skilled in the art and all such alternate embodiments, combinations, modifications, improvements are within the scope of the present invention.

Figure 2:
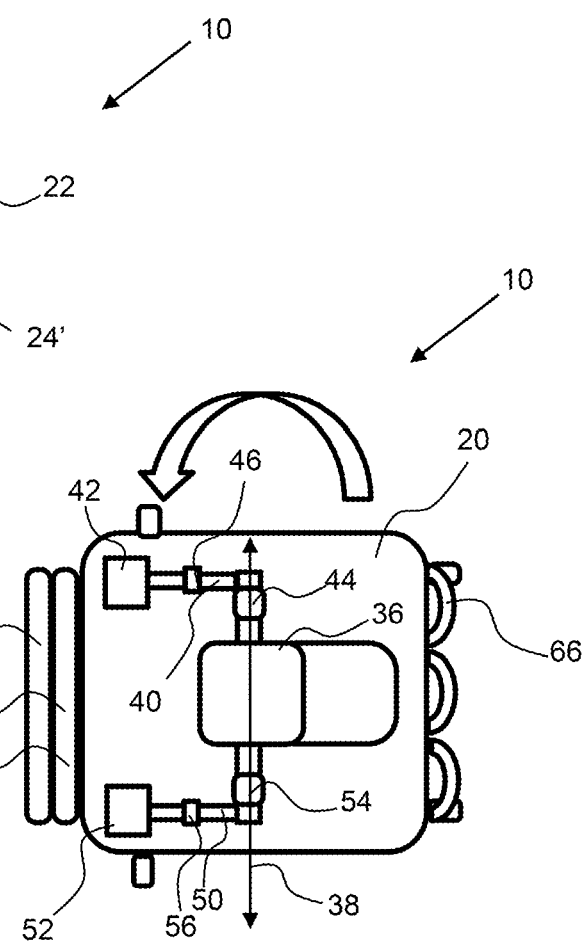
FIG. 2 shows a cross section of the exemplary muscle memory training apparatus having a motor with arms coupled to opposing sides of the motor and having weights coupled to the arms that produce an off-balance force.
Figure 3:
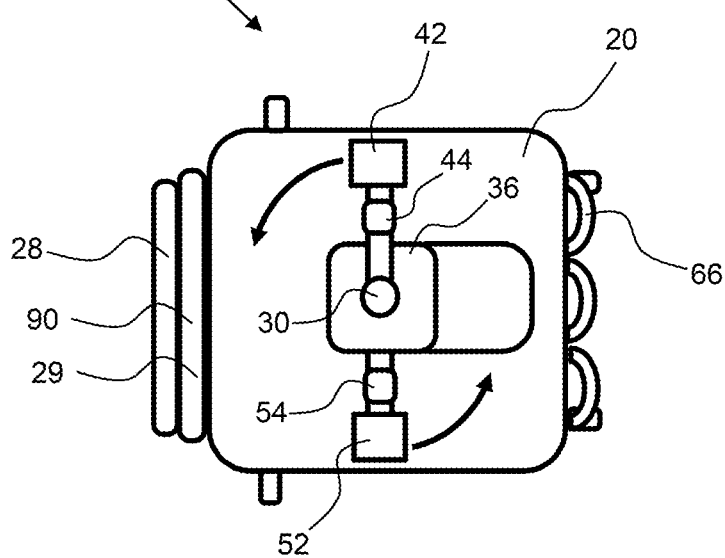
FIG. 3 shows a cross section of the exemplary muscle memory training apparatus shown in FIG. 2, now turned ninety degrees and the first arm and second arm are extending in opposing directions, 180 degrees apart, versus the same rotational orientation in FIG. 2.

Referring now to FIGS. 1 to 3, an exemplary muscle memory training apparatus 10 has a housing 20, which may be an enclosure, for the producing forces to off-balance a person and a plurality of retainers 60, configured to retain a strap that extends from the muscle memory training apparatus to a person. There are a back retainers 66 configured along the back face 26 of the housing 20 and side retainers 64 configured on each of the four side faces 24, 24' 24" and 24"'. Some side retainers are not visible in this view. The front face 22, opposite the back face 26 may have a coupling pad 28 for comfort.

Referring now to FIG. 2, the exemplary muscle memory training apparatus 10 has a motor 36 with a first arm 40 and a second arm 50 extending from the axle 30 and extending in the same direction from the axle. Both the first arm 40 and second arm 50 are configured to be rotationally adjusted about the axle by a respective first arm axle coupler 44 and a second arm axle coupler 54. As shown the arms are extending in the same rotational direction with respect to the axle 30. Each of the arms has a detachably attachable weight, the first arm has a first arm weight 42 attached to the first arm 40 by the first arm weight coupler 46 and the second arm 50 has a second arm weight 52 attached to the second arm 50 by the second arm weight coupler 56. The arms coupled to opposing sides of the motor and having weights coupled to the arms that produce an off-balance force. The muscle memory training apparatus 10 is configured to produce an off-balance force toward and away from the front face 22. On the front face 22 of the housing 20, a coupling plate 29 and coupling pad 28 may be configured. The coupling pad 28 may provide comfort and padding between the housing and a person's back. A coupling plate 28, may be an angle adjustment plate 90 as described herein, enabling the housing to be rotated with respect to the angle adjustment plate 90. The straps, torso strap 70 and shoulder straps as shown in FIGS. 4 and 5 may be coupled with the coupling plate 29 or angle adjustment plate 90.

Referring now to FIG. 3, the exemplary muscle memory training apparatus 10 shown in FIG. 2, is now turned ninety degrees such and the first arm and second arm are now extending in opposing directions, 180 degrees apart, versus the same rotational orientation of the arms as shown in FIG. 2. This change in the orientation of the arms and the rotational orientation of the housing will produce different off-balancing forces. A person may don the muscle memory training apparatus 10 is a first orientation as shown in FIG. 2 and perform activities and then switch one of the arms and rotate the housing 20, 90 degrees and don the muscle memory training apparatus 10 as shown in FIG. 2 and perform activities to strengthen their neuromuscular plasticity system and strength muscle memory.

Figure 4:
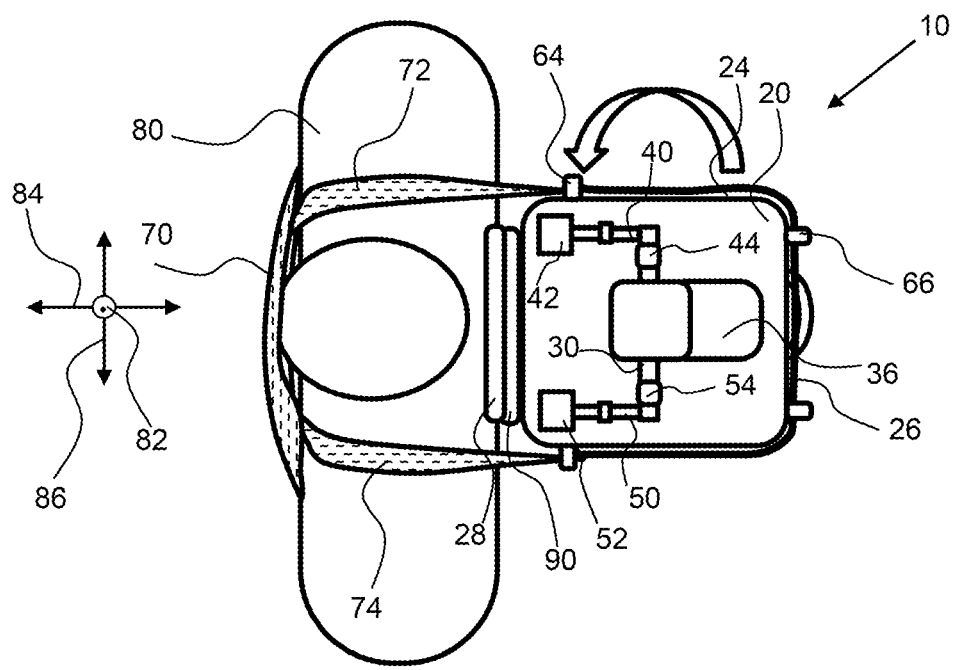
FIG. 4 shows a top view of a person with the exemplary muscle memory training apparatus strapped to their back and the arms spinning with the arm weights attached to produce an off-balancing force along a longitudinal axis (vertical with respect to the person standing) and sagittal axis (front to back).
Figure 5:
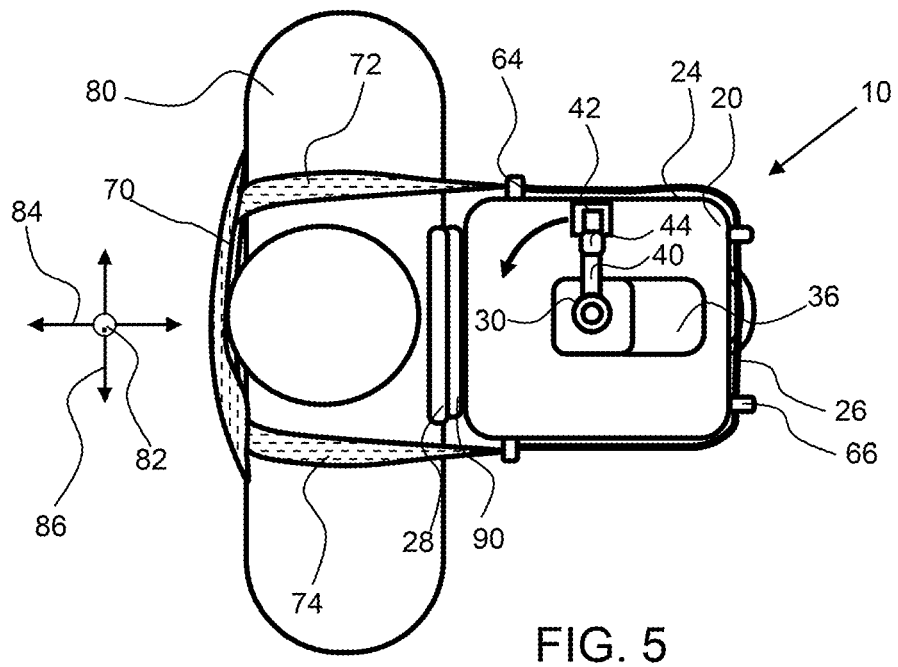
FIG. 5 shows a top view of a person with the exemplary muscle memory training apparatus strapped to their back as shown in FIG. 4, now with the muscle memory training apparatus rotated 90 degrees with the arm spinning in a frontal axis (side to side) and sagittal axis (front to back).
Figure 6:
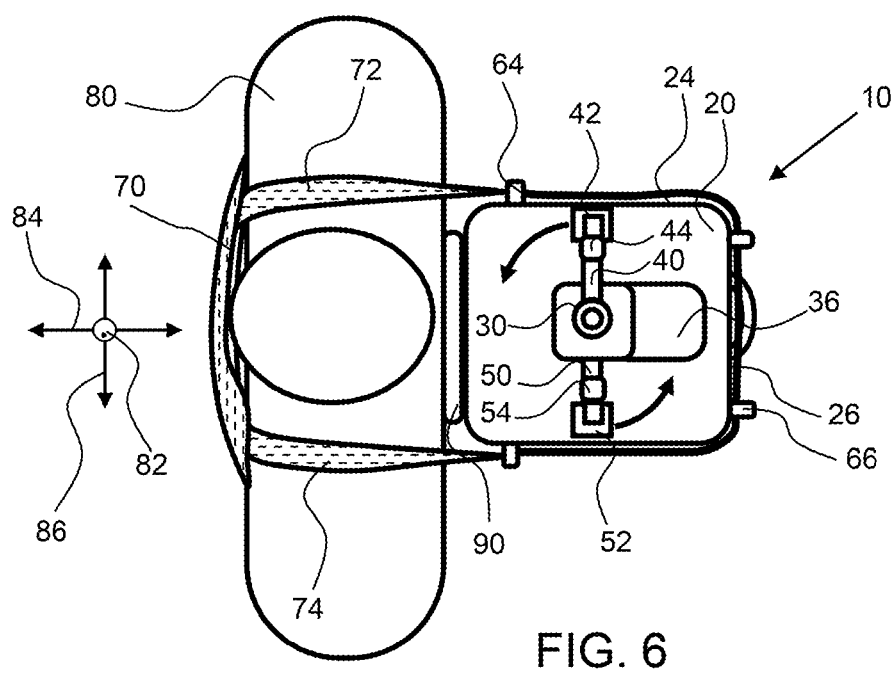
FIG. 6 shows a top view of a person with the exemplary muscle memory training apparatus strapped to their back as shown in FIG. 5, now with the first arm and second arm extending in opposing directions from the axle, wherein the first arm extends 180 degrees from the second arm from the axle.

Referring now to FIGS. 4 to 6, a person 80 has the exemplary muscle memory training apparatus 10 strapped to their back by the first shoulder strap 72, the second shoulder strap 74 and the torso strap 70, that extends around the persons chest or waist, for example. The straps extend through side retainer 64 on opposing sides of the housing 20 and around the back side 26 of the housing 20 through a pair of back retainers 66 to effectively restrain the housing to the person's back with the coupling pad 28, configured therebetween. The motor 36 is rotating the first arm 40 and second arm 50 with the respective first arm weight 42 and second arm weight 52 attached thereto to produce an off-balancing force along a longitudinal axis 82 (vertical with respect to the person standing) and sagittal axis 84 (front to back with respect to the person standing) in FIG. 4 and along a frontal axis 86 (side to side with respect to the person standing) in FIG. 5. The orientation of the muscle memory training apparatus 10 in FIG. 4 is like that shown in FIG. 2 and the orientation in FIG. 5 is like that shown in FIG. 3.

The perturbation portion 21 has been rotated 90 degrees about the sagittal axis 84 from FIG. 4 to FIG. 5. In FIG. 4, the axle 30 extends in the frontal axis 86 or generally horizontally with the person standing erect on a horizontal surface with the exemplary muscle memory training apparatus 10. In FIG. 5, the axle 30 extends vertically or along the longitudinal axis 82. As described herein, the perturbation portion 21 may be configured to rotation with respect to angle adjustment plate 90.

As shown in FIG. 6, the exemplary muscle memory training apparatus 10 is strapped to the back of a person 80 (user) as shown in FIG. 5, now with the first arm and second arm extending in opposing directions from the axle, wherein the first arm extends 180 degrees from the second arm from the axle. This configuration may produce a twisting force with one weight pushing forward while the opposing weight on the second arm producing a pulling force, or force away from the user.

Referring now to FIGS. 7 to 13, a person has an exemplary muscle memory training apparatus 10 strapped to their back to produce an off-balancing force that they must accommodate for while they attempt to perform a task, such as tracing a circle or figure eight with their outstretched arm. As shown in each of FIGS. 7 to 13, the muscle memory training apparatus is secured to the person by a first shoulder strap 72 and a second shoulder strap 74 and a torso strap 70. The straps extend through a side retainer 64 on a side 24 of the housing 20 and a pair of back retainers 66 on a back 26 of the housing 20.

Figure 7:
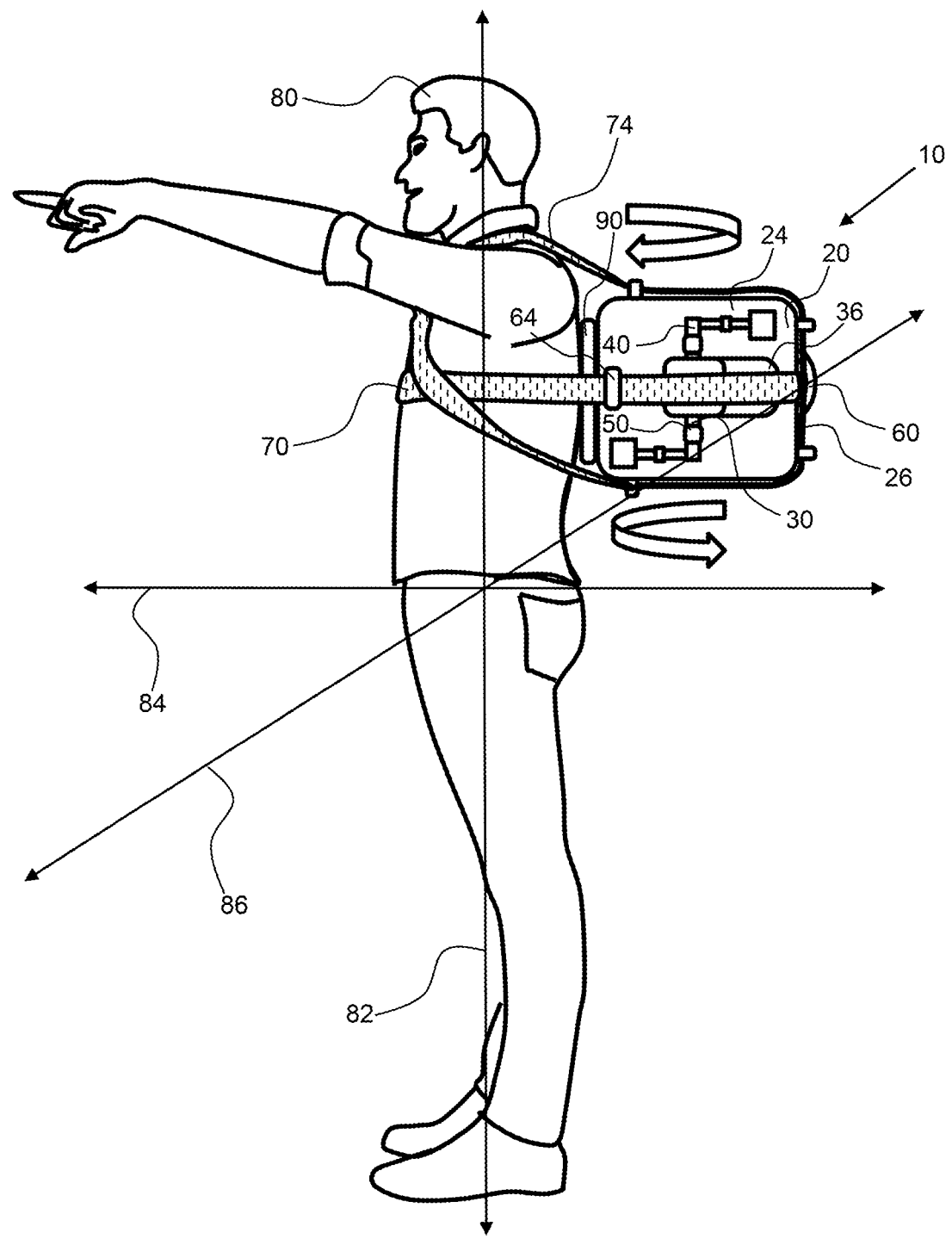
FIG. 7 shows a side view of a person with the exemplary muscle memory training apparatus strapped to their back with the arms extending 180 degrees apart as shown in FIG. 6 and the arms spinning with the arm weights attached to produce perturbation forces along a frontal axis (side to side) and sagittal axis (front to back).

As shown in FIG. 7, the axle 30 of the motor 36 extends vertically or along the longitudinal axis 82 with the person standing upright on a horizontal surface. The first arm 40 and second arm 50 are configured 180 offset from each other with respect to the axle 30. The motor spins the two weights to produce an off-balancing force in the sagittal axis 84 (front to back) and also in the longitudinal axis (up and down).

Figure 8:
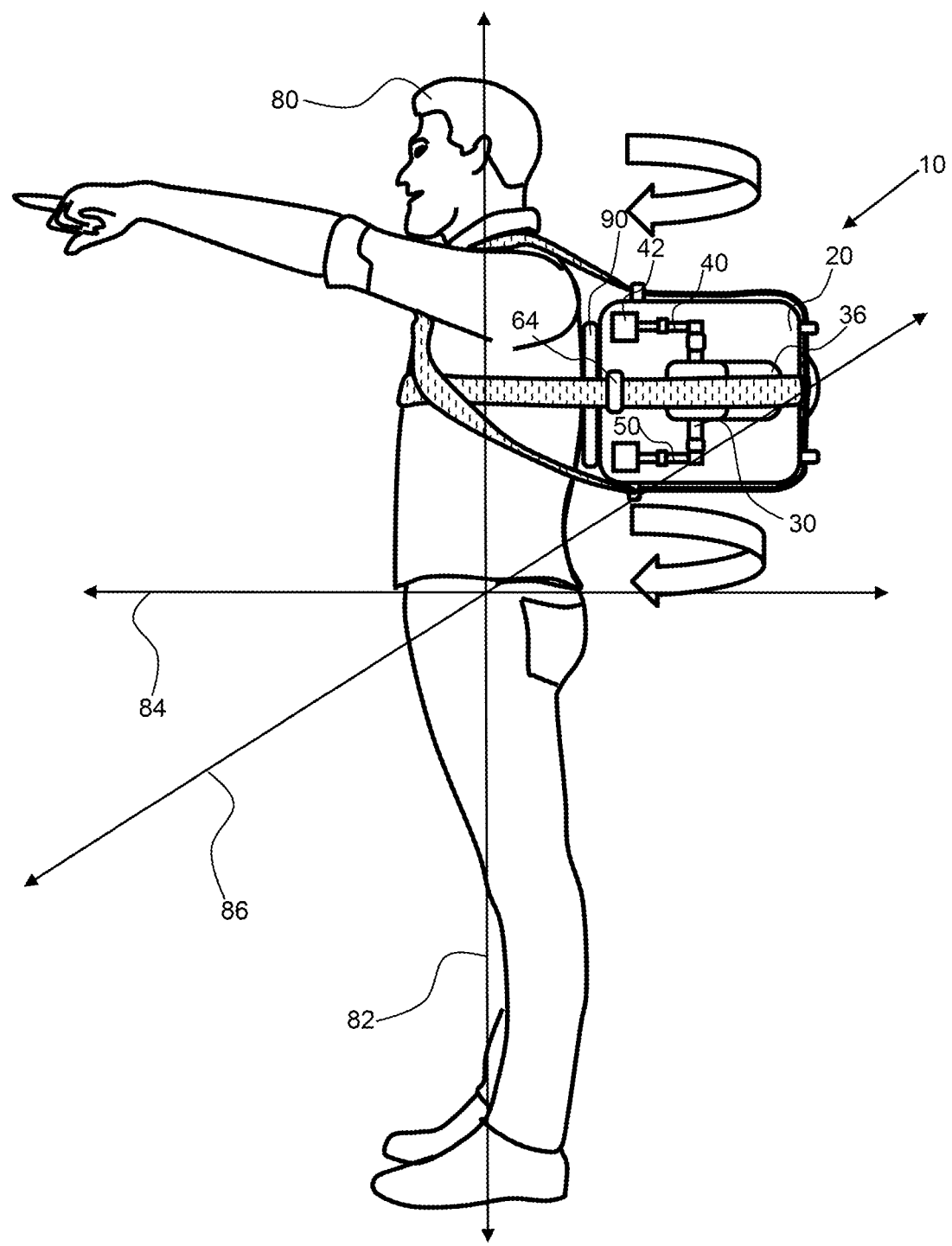
FIG. 8 shows a side view of a person with the exemplary muscle memory training apparatus strapped to their back as shown in FIG. 7, with the arms now extending in the same direction from the axle to produce a stronger off balancing force.

As shown in FIG. 8, the axle 30 of the motor 36 extends vertically or along the longitudinal axis 82 with the person standing upright on a horizontal surface. The first arm 40 and second arm 50 extend radially from the axle in alignment with each other. The motor spins the two weights to produce an off-balancing force in the sagittal axis 84 (front to back) and also side to side. This configuration may produce a stronger off-balance force as the weights are aligned with each other.

Figure 9:
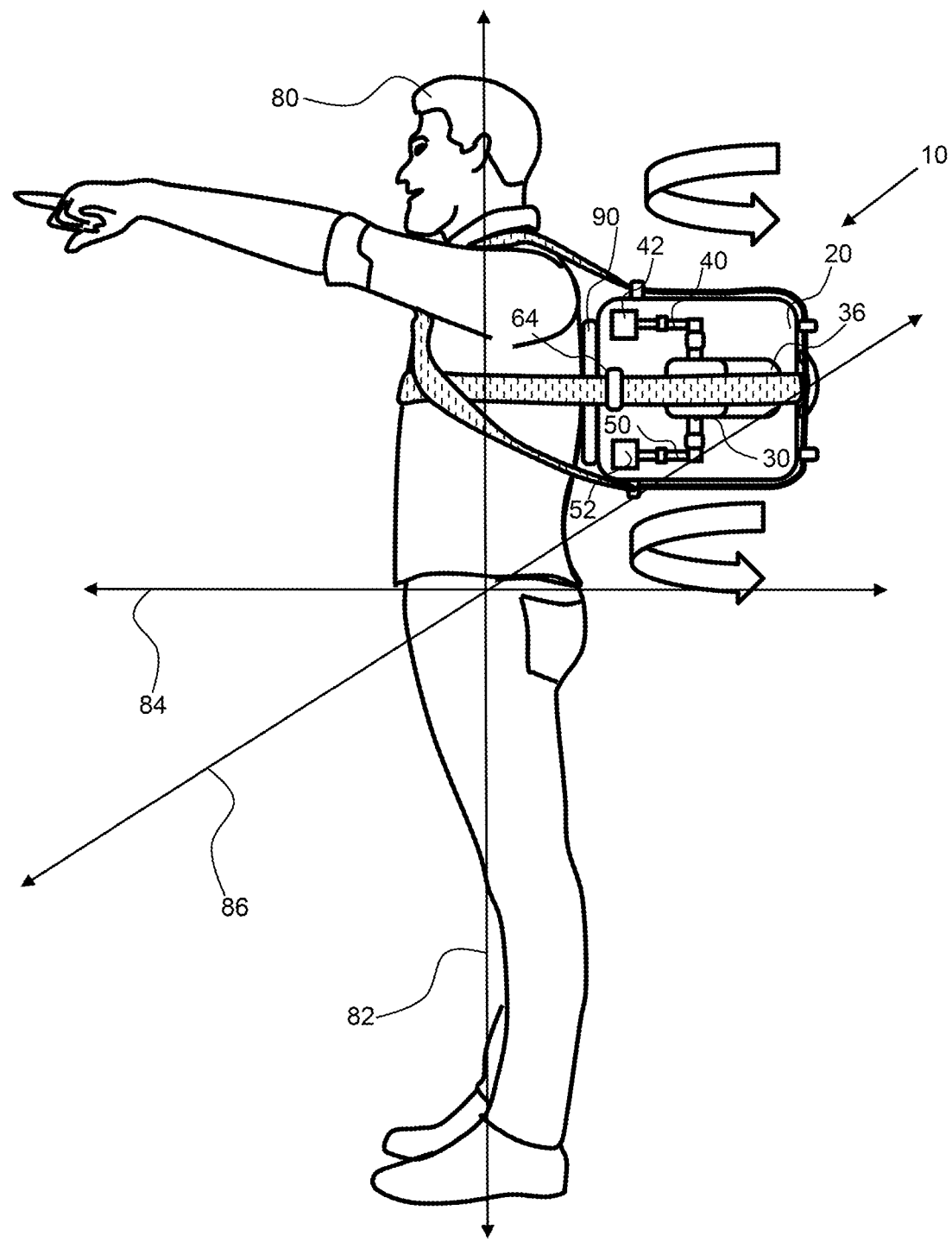
FIG. 9 shows a side view of a person with the exemplary muscle memory training apparatus strapped to their back as shown in FIG. 8, with the arms now rotating in an opposite direction from the direction shown in FIG. 8.

As shown in FIG. 9, the axle 30 of the motor 36 extends vertically or along the longitudinal axis 82 with the person standing upright on a horizontal surface. The first arm 40 and second arm 50 extend radially from the axle in alignment with each other. The motor spins the two weights to produce an off-balancing force in the sagittal axis 84 (front to back). This configuration shows that the direction of rotation of the motor may be reversed, wherein the rotation direction in FIG. 9 is opposite the direction of rotation shown in FIG. 8.

Figure 10:
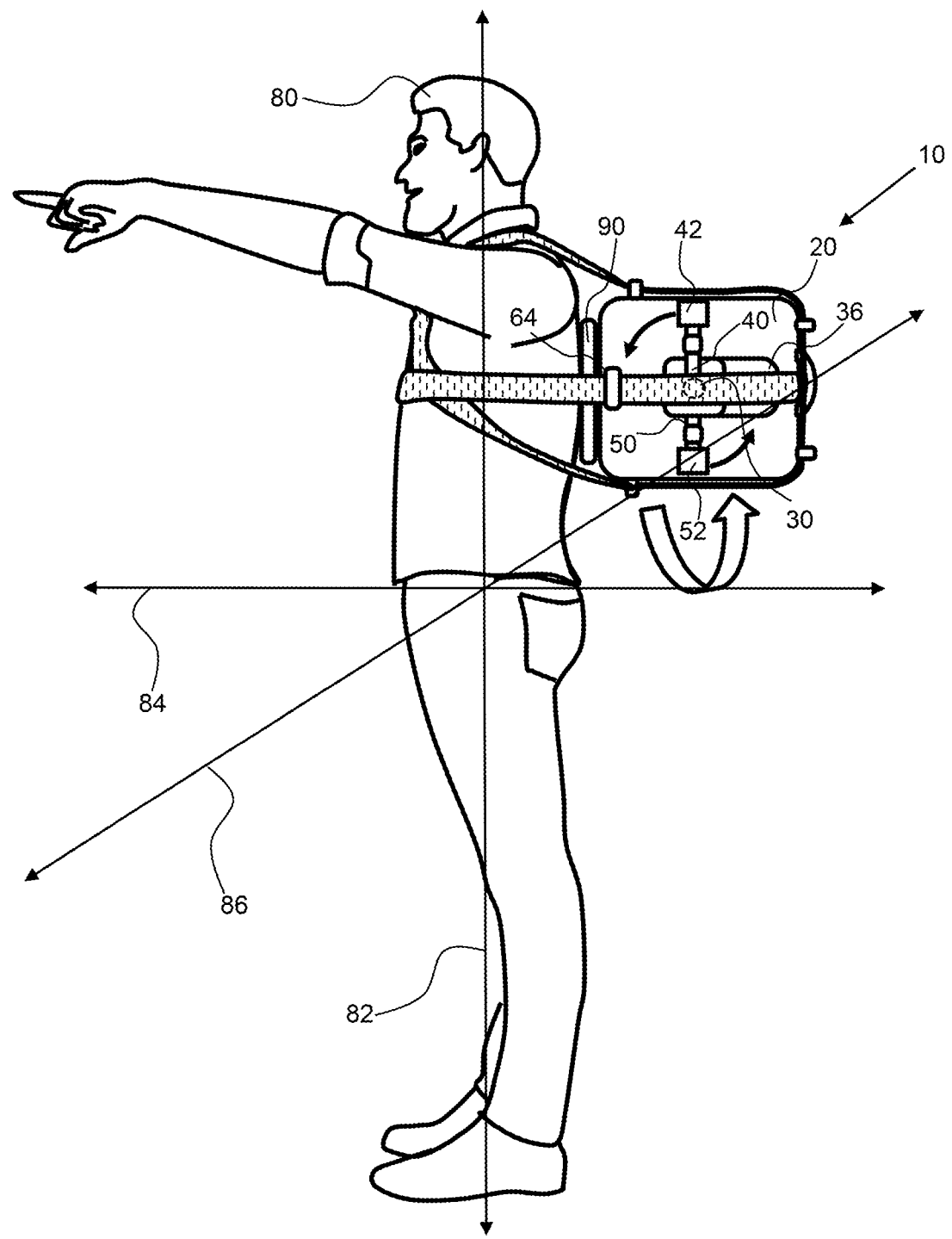
FIG. 10 shows a side view of a person with the exemplary muscle memory training apparatus strapped to their back as shown in FIG. 2, with the arms now extending in opposing directions from the axle.

As shown in FIG. 10, the axle 30 of the motor 36 extends horizontally or along the sagittal axis 84 with the person standing upright on a horizontal surface. The first arm 40 and second arm 50 extend radially from the axle 30 in opposing directions of offset 180 degrees. The motor spins the first arm weight 42 and second arm weight 52 to produce an off-balancing force in the sagittal axis 84 (front to back) to produce both an off-balancing force in the sagittal axis 84 and longitudinal axis 82.

Figure 11:
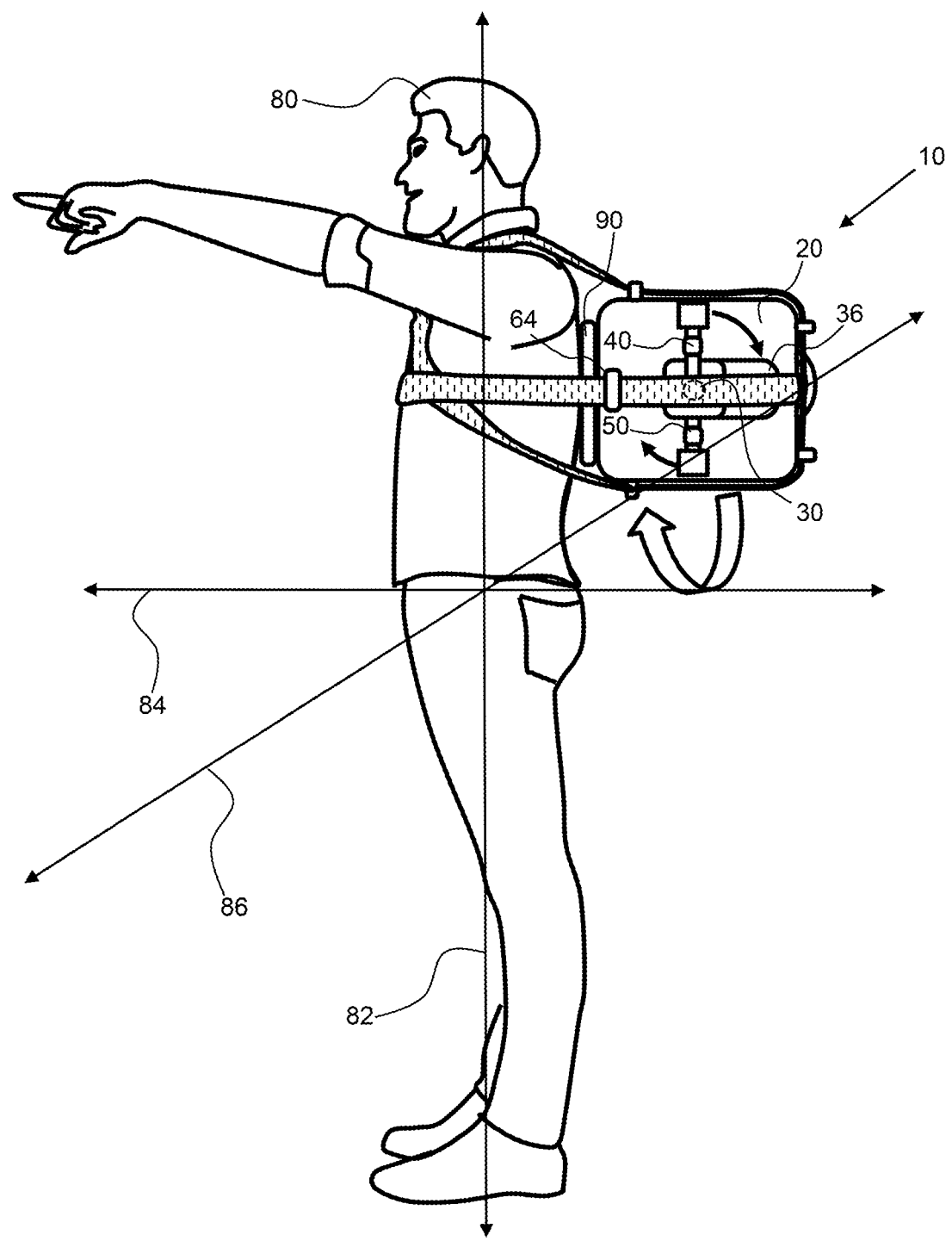
FIG. 11 shows a side view of a person with the exemplary muscle memory training apparatus strapped to their back as shown in FIG. 10, with the arms now rotating in an opposite direction from the direction shown in FIG. 10.

As shown in FIG. 11, the motor 36 spins the first arm weight 42 and second arm weight 52 in an opposite direction from that shown in FIG. 10, to produce an off-balancing force in the sagittal axis 84 (front to back) to produce both an off-balancing force in the sagittal axis 84 and longitudinal axis 82.

Figure 12:
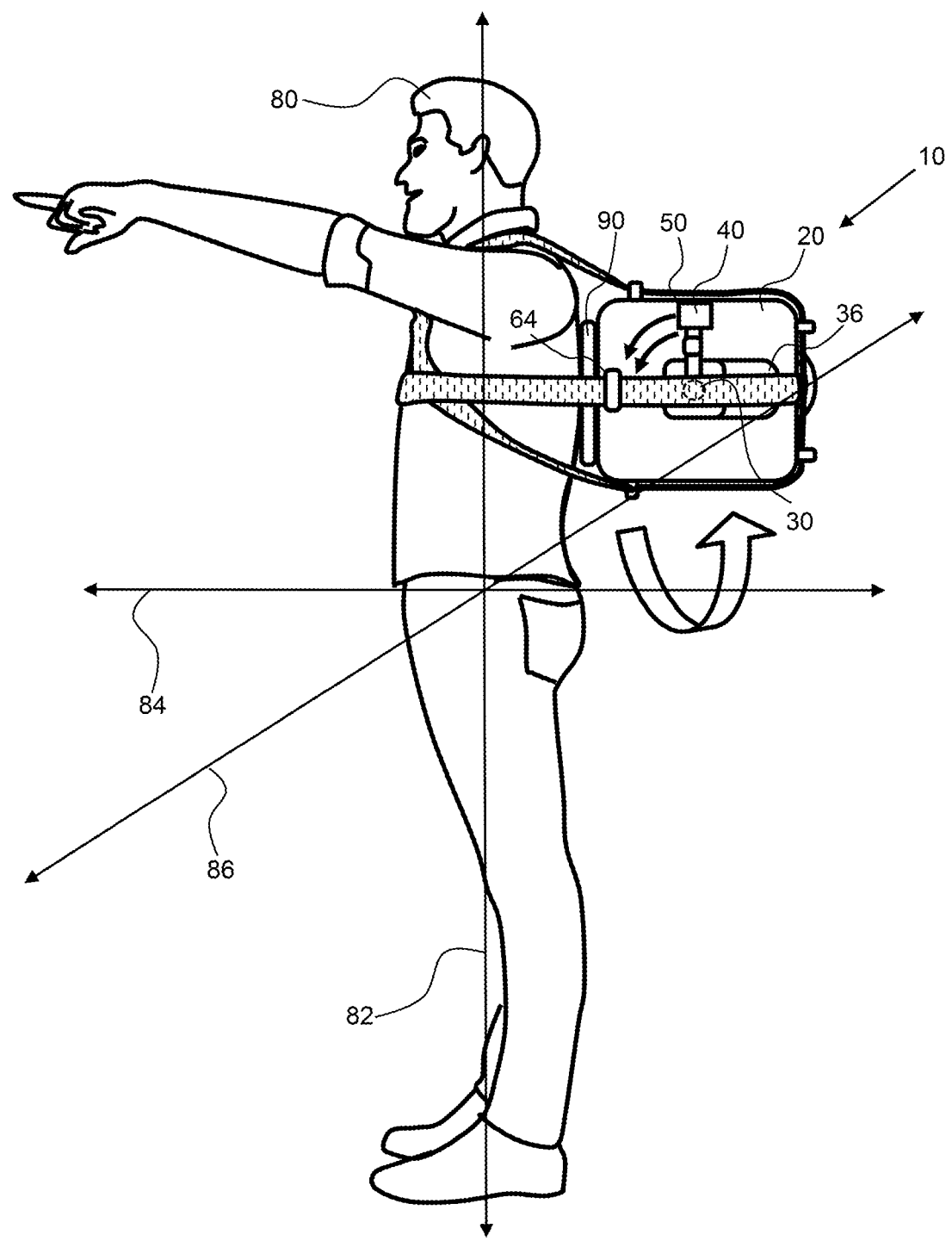
FIG. 12 shows a side view of a person with the exemplary muscle memory training apparatus strapped to their back as shown in FIG. 10, with the arms now extending in the same directions from the axle.

As shown in FIG. 12, the axle 30 of the motor 36 extends horizontally or along the sagittal axis 84 with the person standing upright on a horizontal surface. The first arm 40 and second arm 50 extend radially from the axle 30 in the same direction, or in radially alignment from the axle. The weights therefore spin in unison together about the axle to produce both an off-balancing force in the sagittal axis 84 and longitudinal axis 82. This configuration may produce a stronger off-balance force as the weights are aligned with each other.

Figure 13:
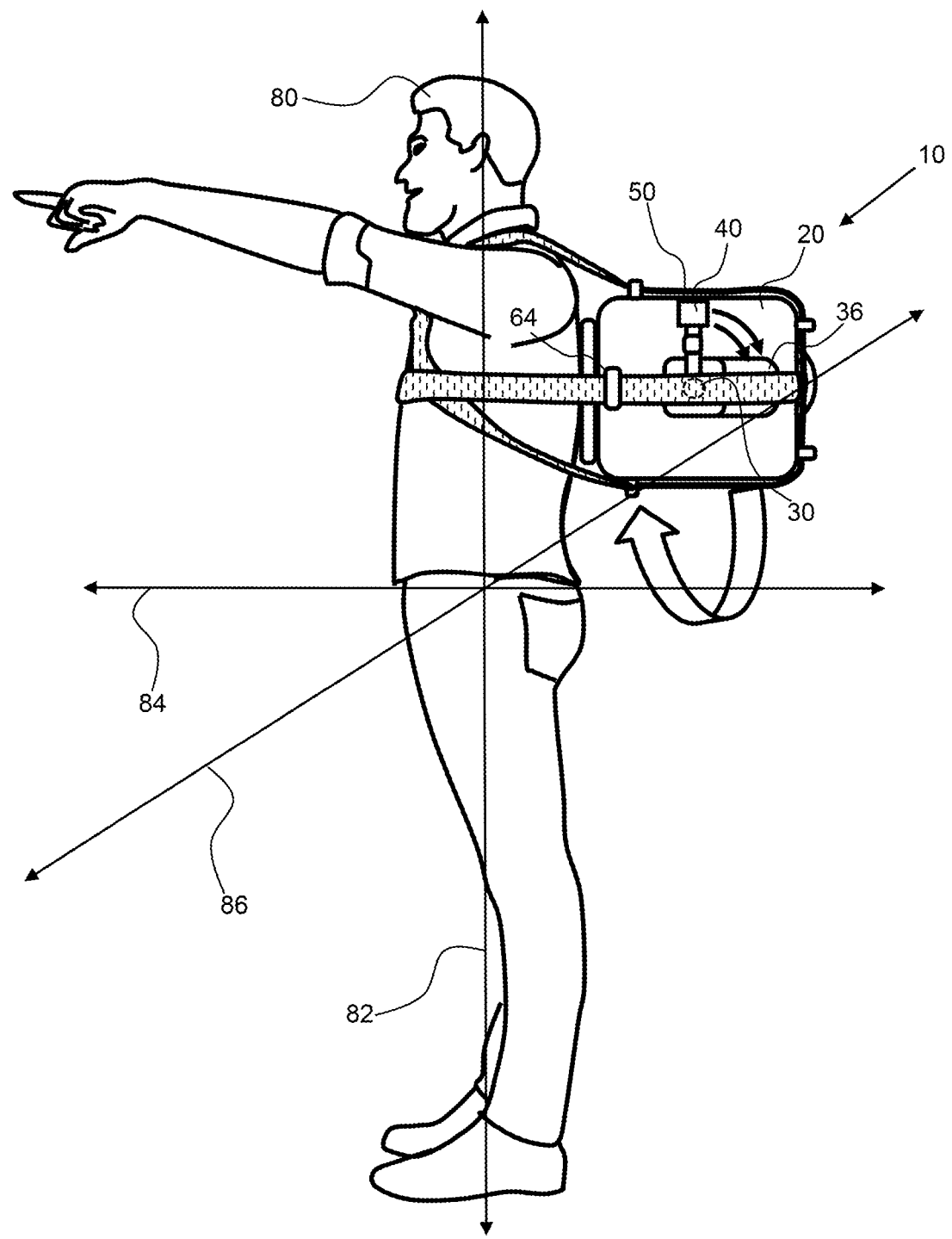
FIG. 13 shows a side view of a person with the exemplary muscle memory training apparatus strapped to their back as shown in FIG. 12, with the arms now rotating in an opposite direction from the direction shown in FIG. 12.

As shown in FIG. 13, the motor 36 spins the first arm weight 42 and second arm weight 52 in an opposite direction from that shown in FIG. 1, to produce both an off-balancing force, a perturbating force at a perturbating frequency in the sagittal axis 84 and longitudinal axis 82. The perturbating force on a person retrains said reflex stabilization muscle memories by practicing said reflex stabilization muscle memories to the perturbating force while performing voluntary muscle movements, such as trying to point at an object.

Figure 14:
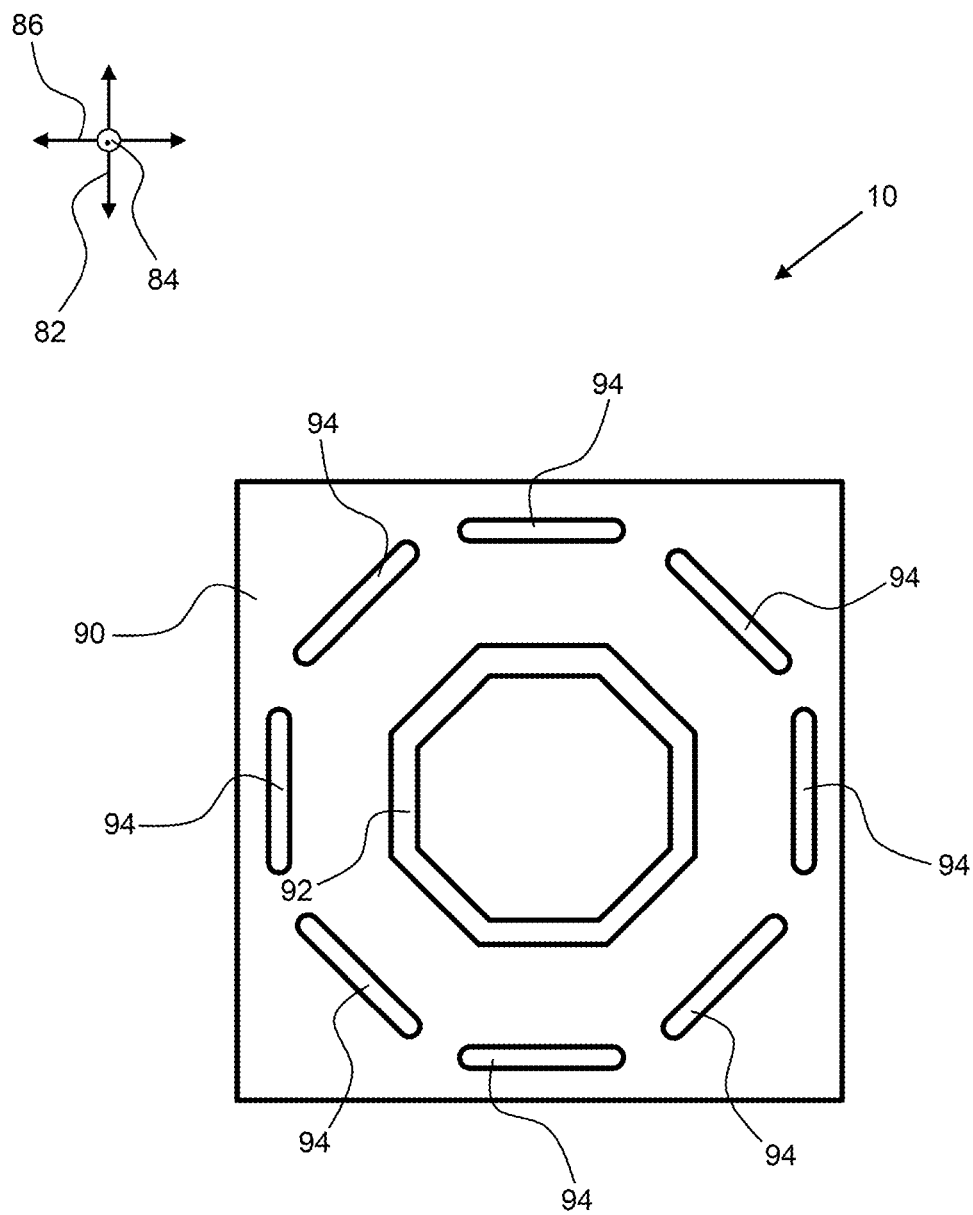
FIG. 14 shows a front view of an angle adjustment plate of a muscle memory training apparatus.
Figure 15:
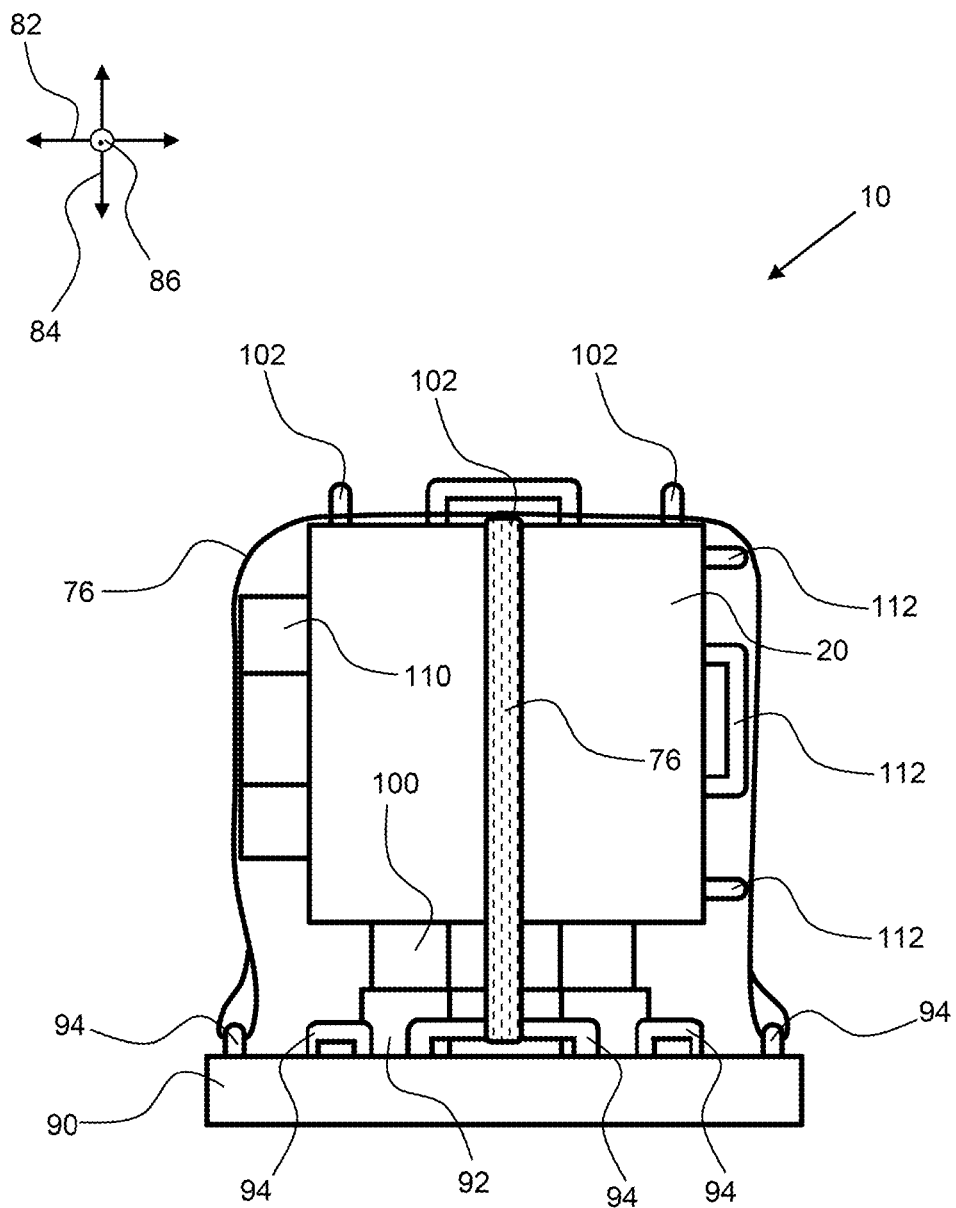
FIG. 15 shows a side view of a housing of a muscle memory training apparatus connected to an angle adjustment plate by a first angle adjustment protrusion, an interconnect portion, and straps.

As shown in FIG. 14, an angle adjustment plate 90 has an interconnect portion 92 that is configured to couple with the housing 20 of the perturbation portion 21 of the muscle memory training apparatus 10, shown in FIG. 15. The interconnect portion 92 shown in FIG. 14 has a plurality of sides, such as eight sides to enable adjustable angular orientation with the adjustable plate. The eight sides enable adjustment at 45, 90 135, 180, 225, 270 and 360 degrees. Angle adjustment plate retainers 94 are configured on the angle adjustment plate 90 around the interconnect portion 92 and may be slots configured to retain a strap. There are eight angle adjustment plate retainers 94, which corresponds with the eight sides of the interconnect portion 92.

As shown in FIG. 15, a first angle adjustment feature 100, such as a protrusion, extends from the housing 20 of perturbation portion 21 of the muscle memory training apparatus 10. A second angle adjustment feature 110 extends from the housing 20 from a separate face of the housing 20, and extends orthogonally from the extension direction of the first angle adjustment feature 100. The first angle adjustment feature 100 and the second angle adjustment feature 110 each have eight sides, which correlate with the eight sides of the interconnect portion 92. The second angle adjustment feature 110 extends orthogonal to the first angle adjustment feature 100. First angle adjustment retainers 102 extend from the housing 20 opposite the first angle adjustment feature 100. Second angle adjustment retainers 112 extend from the housing 20 opposite the second angle adjustment feature 110.

The first angle adjustment feature 100 is received by the interconnect portion 92 of the angle adjustment plate 90 to removably connect the housing 20 to the angle adjustment plate 90. The housing 20 is secured to the angle adjustment plate 90 by straps 76 that are configured through the first angle adjustment retainers 102 and the angle adjustment plate retainers 94. Two straps 76 are used to secure the housing 20 to the angle adjustment plate 90. These two straps 76 are configured orthogonal to one another.

The orientation of the housing 20 may be adjusted by removing the housing 20 or perturbation portion 21, from the angle adjustment plate 90, rotating the housing 20 about at least one of the sagittal axis 84, longitudinal axis 82 and frontal axis 86, and reconnecting the housing 20 to the angle adjustment plate 90 by receiving the first angle adjustment feature 100 with the interconnect portion 92 and securing the housing 20 to the angle adjustment plate 90 by configuring the straps 76 through the first angle adjustment retainers 102 and the angle adjustment plate retainers 94.

The orientation of the housing 20 may also be adjusted by removing the housing 20 from the angle adjustment plate 90 and rotating the housing 20 about the frontal axis 86 whereby the second angle adjustment feature 110, such as a protrusion, is aligned with the interconnect portion 92. The housing 20 may be reconnected to the angle adjustment plate 90 by receiving the second angle adjustment feature 110 with the interconnect portion and securing the housing 20 to the angle adjustment plate 90 by configuring the straps 76 through the second angle adjustment retainers 112 and the angle adjustment plate retainers 94.

Figure 16:
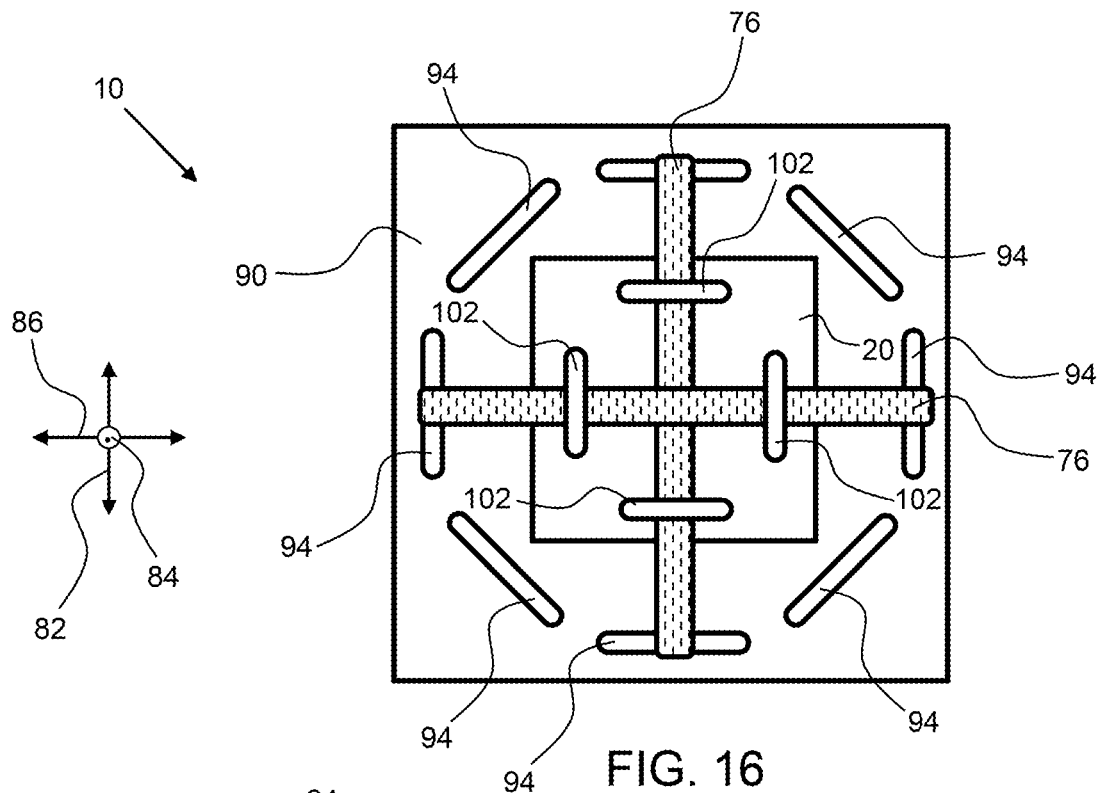
FIG. 16 shows a top view of a housing of a muscle memory training apparatus configured relative to an angle adjustment plate.
Figure 17:
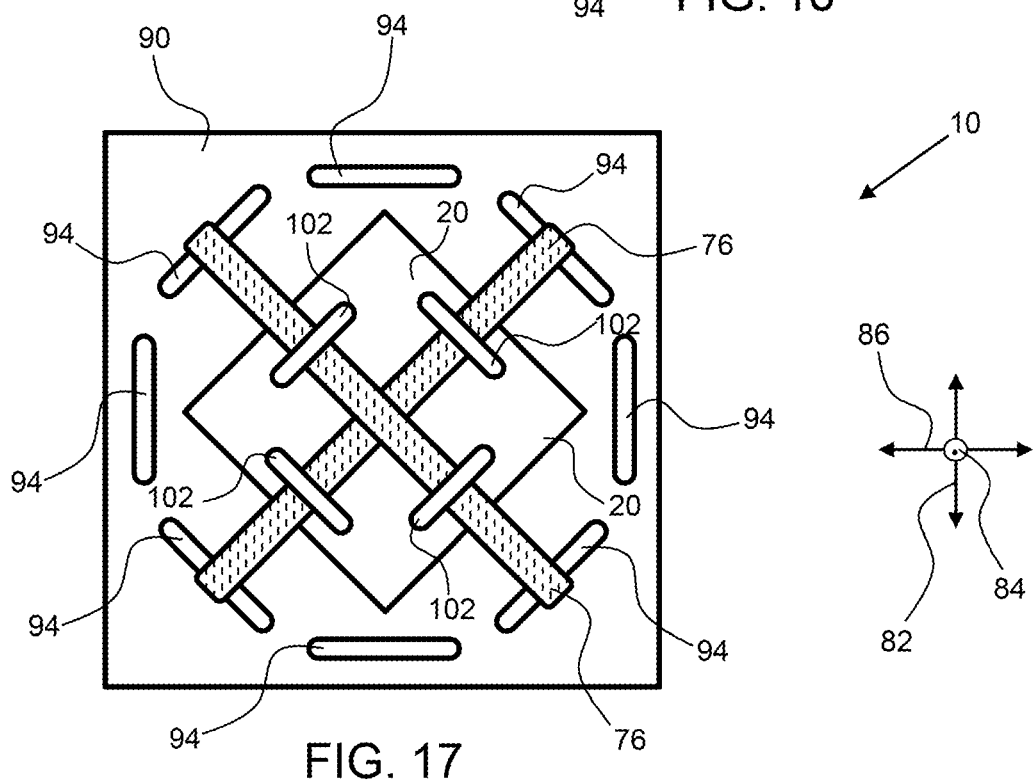
FIG. 17 shows the muscle memory training apparatus of FIG. 16 wherein the housing is oriented at a different angle relative to the angle adjustment plate.

As shown in FIG. 16, the housing 20 is configured relative to the angle adjustment plate 90. The housing 20 is secured to the angle adjustment plate 90 by straps 76 that are configured through the first angle adjustment retainers 102 and the angle adjustment plate retainers 94. As shown in FIG. 17, the housing 20 of FIG. 16 is configured at a different angle relative to the angle adjustment plate by rotating the housing 20 about the sagittal axis 84. As shown in FIG. 17, the housing 20 is secured to the angle adjustment plate 90 by straps 76 that are configured through the first angle adjustment retainers 102 and angle adjustment plate retainers 94. Since the orientation of the housing 20 is different in FIG. 17 than in FIG. 16, the straps 76 in FIG. 17 are configured through different angle adjustment plate retainers 94 than in FIG. 16 to allow for the housing 20 to be secured in its different orientation.

Figure 18:
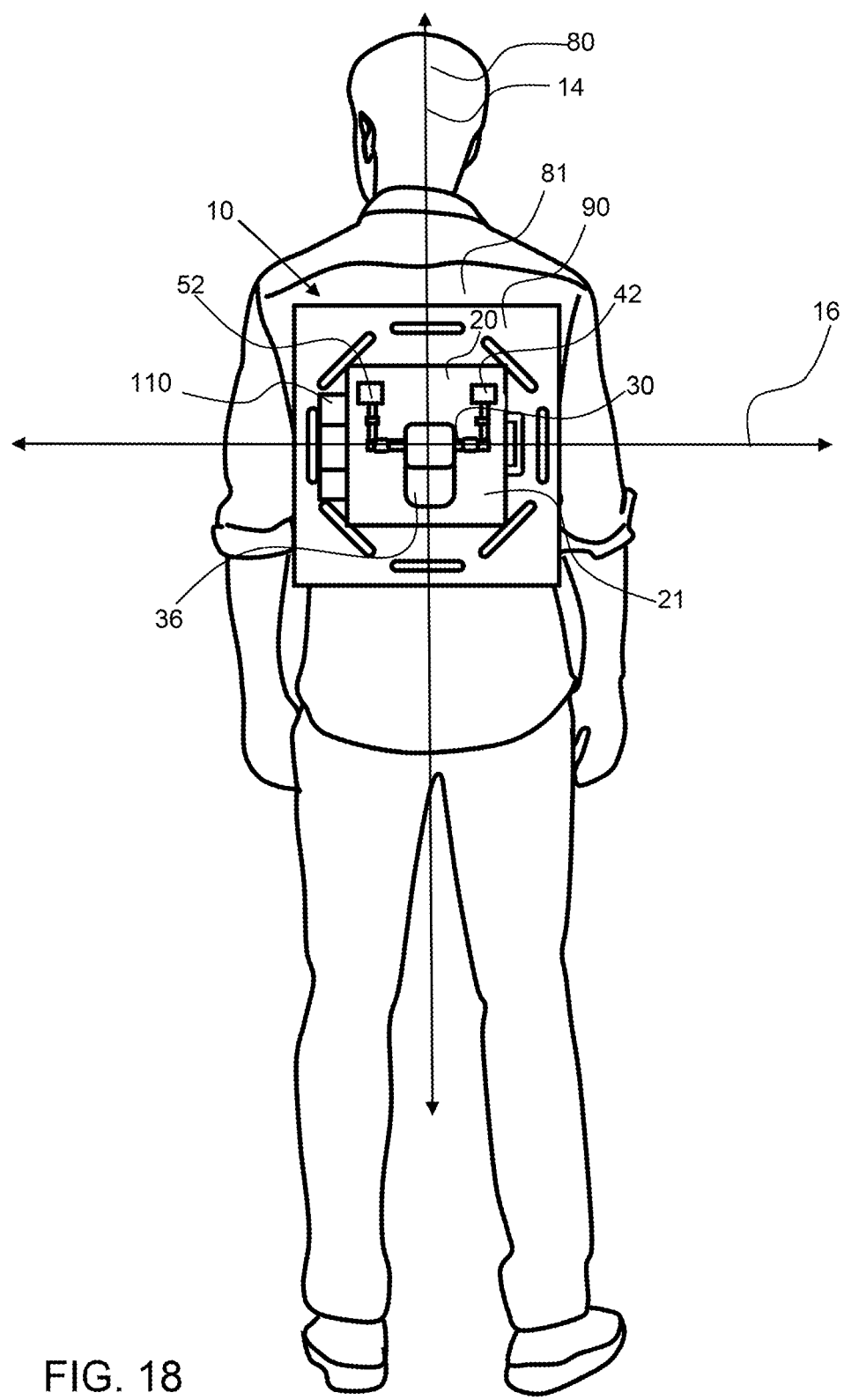
FIG. 18 shows a back view of a person with the muscle memory training apparatus configured on their back with the axle extending horizontally across the person's back and with the first arm and the second arm oriented in the same rotational direction from the axle.
Figure 19:
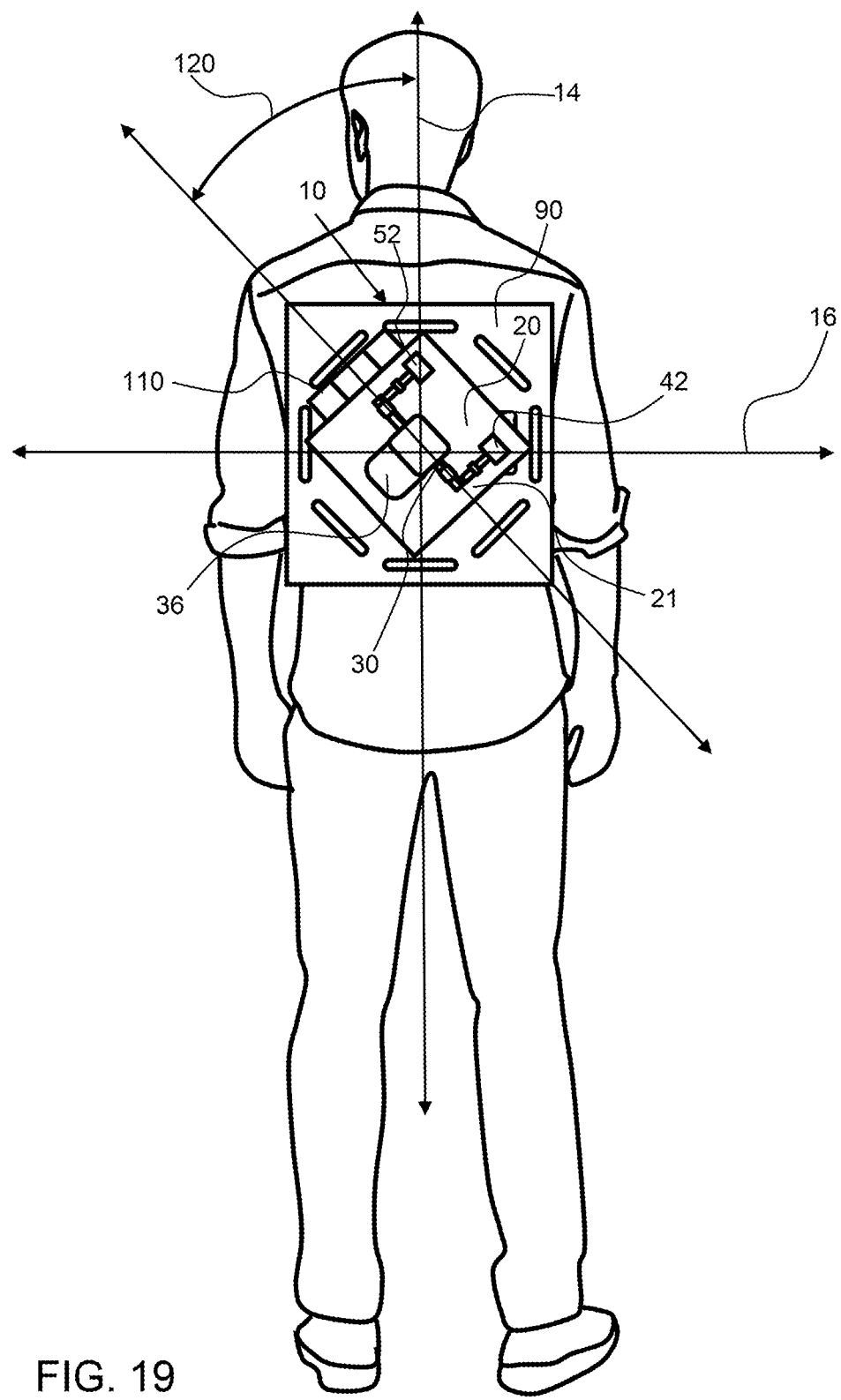
FIG. 19 shows a back view of a person with the muscle memory training apparatus configured on their back with the axle extending at an offset angle to vertical across the person's back; wherein the first angle adjustment protrusion has been rotated to configure the perturbation portion at said offset angle.
Figure 20:
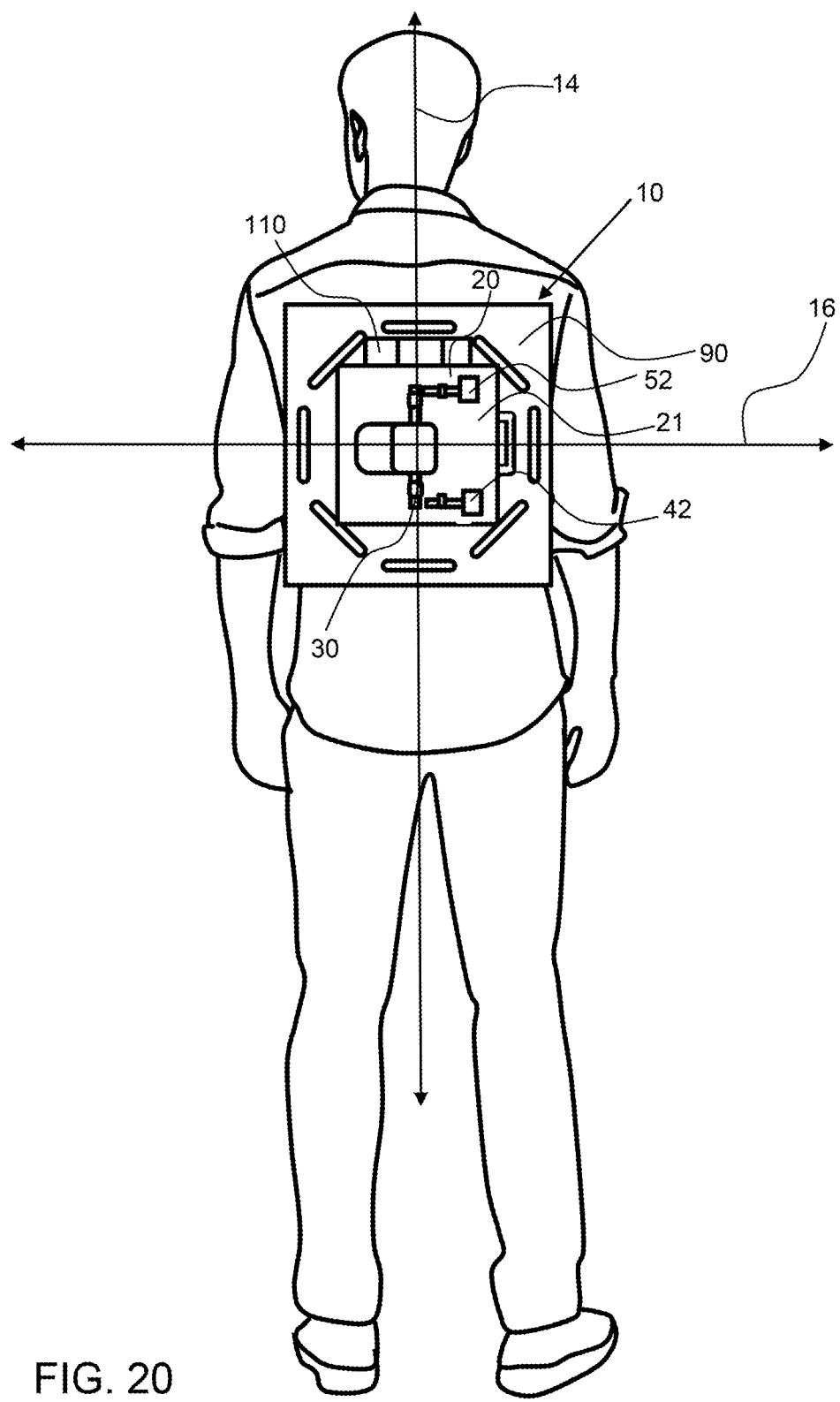
FIG. 20 shows a back view of a person with the muscle memory training apparatus configured on their back with the axle extending vertically along the person's back and with the first arm and the second arm oriented in the same rotational direction from the axle.
Figure 21:
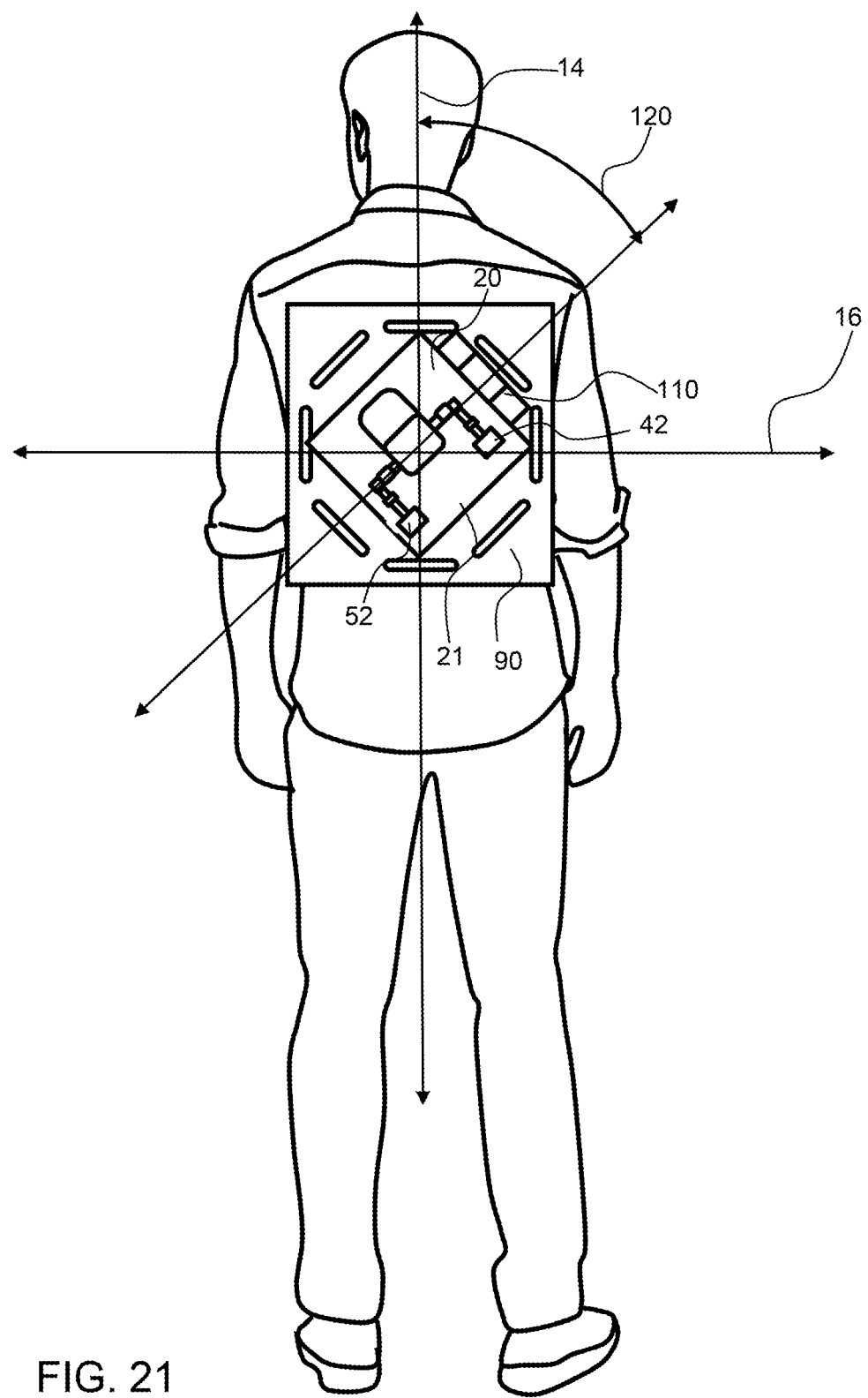
FIG. 21 shows a back view of a person with the muscle memory training apparatus configured on their back with the axle extending at an offset angle to vertical across the person's back; wherein the first angle adjustment protrusion has been rotated to configure the perturbation portion at said offset angle

Referring now to FIGS. 18 to 21, a person 80 has a muscle memory training apparatus 10 configured on their back with perturbation portion 21 configured in different rotational orientations with respect to the angle adjustment plate 90 via the first angel adjustment portion engaged with the angle adjustment plate 90. As shown in FIG. 18, the perturbation portion 21 is configured with the axle 30 extending horizontally across the person's back, or along a horizontal axis 16, and with the first arm 40 and the second arm 50 oriented in the same rotational direction from the axle. As shown in FIG. 19, the perturbation portion 21 is configured with the axle 30 extending at an offset angle 120 from the vertical axis 14 across the person's back 81, and with the first arm 40 and the second arm 50 oriented in the same rotational direction from the axle. The offset angle 120 is measured from the vertical axis 14. The perturbation portion 21 will produce a force that is offset from the vertical axis 14 and horizontal axis 16 in this configuration. The first angle adjustment protrusion (not shown) has been engaged with the angle adjustment plate 90. As shown in FIG. 20, the perturbation portion 21 is configured with the axle 30 extending vertically across the person's back, or along a vertical axis 14, and with the first arm 40 and the second arm 50 oriented in the same rotational direction from the axle. As shown in FIG. 21, the perturbation portion 21 is configured with the axle 30 extending at an offset angle 120 from the vertical axis 14 with the first arm 40 and the second arm 50 oriented in the same rotational direction from the axle. The offset angle 120 is measured from the vertical axis 14. The perturbation portion 21 will produce a force that is offset from the vertical axis 14 and horizontal axis 16 in this configuration. The first angle adjustment protrusion (not shown) has been engaged with the angle adjustment plate 90. Note that the offset angle has the same value but is to the opposing side of the vertical axis 14 from the perturbation portion 21 shown in FIG. 19.

Figure 22:
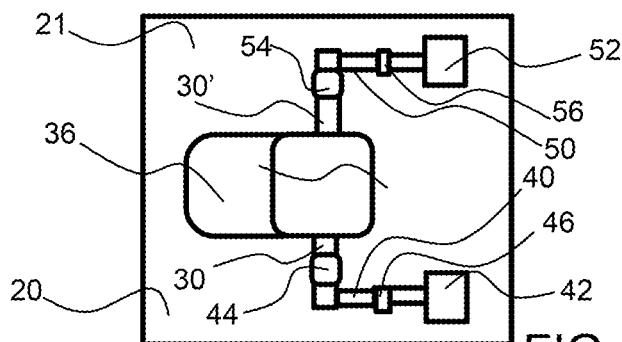
FIG. 22 shows a diagram of a perturbation portion of a muscle memory training apparatus having the first arm and second arm configured in the same rotational position with respect to the axle.

Referring now to FIGS. 22 to 25, a perturbation portion 21 of a muscle memory training apparatus 10 has a variety of adjustments in the arms and weights coupled to the axle 30. The first and second arms can be rotated about the axle and locked into a desired rotational position, such as having the arms extending in the same rotational position or opposing rotational positions, or about 180 degrees separated (within 15 degrees of 180 degrees). Also, the magnitude of the weight attached can be changed, as well as the has the first arm 40 and second arm 50 configured in the same rotational position with respect to the axle 30. As shown in FIG. 22, the first arm 40 and the second arm 50 are configured or extend in the same rotational orientation from the axle 30. Also, the first arm weight 42 and the second arm weight 52 may weight substantially the same within about 5%. For example, an exemplary perturbation portion 21 has a first arm weight 42 that weighs 0.5 kg and a second arm weight 52 that weighs 0.5 kg (+/−0.025 kg); thereby being substantially the same weight. Finally, the distance of the arm weight arm may be changed to produce a higher torque force as the weight is spun around the axle.

As shown in FIG. 22, a perturbation portion 21 of a muscle memory training apparatus 10 has the first arm 40 and second arm 50 configured in the substantially the same rotational position with respect to the axle 30, wherein the first arm extends from the axle in the same rotational orientation (within about 10 degrees) as the second arm. Also, the first arm weight 42 and second arm weight 52 are substantially the same weight and the first arm weight is configured substantially the same offset distance from the axle (within about 10%) as the second arm weight.

Figure 23:
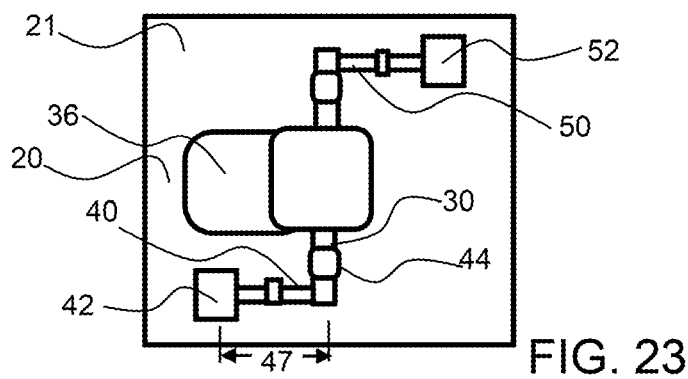
FIG. 23 shows a diagram of a perturbation portion of a muscle memory training apparatus having the first arm and second arm configured in opposing rotational position with respect to the axle, wherein the first arm extends from the axle 180 degrees from the second arm.

As shown in FIG. 23, a perturbation portion 21 of a muscle memory training apparatus 10 has the first arm 40 configured in a substantially opposing rotational position as the second arm 50 or about 180 degrees (within about 10 degrees of 180 degrees). Also, the first arm weight 42 and second arm weight 52 are substantially the same weight and the first arm weight is configured substantially the same offset distance from the axle (within about 10%) as the second arm weight.

Figure 24:
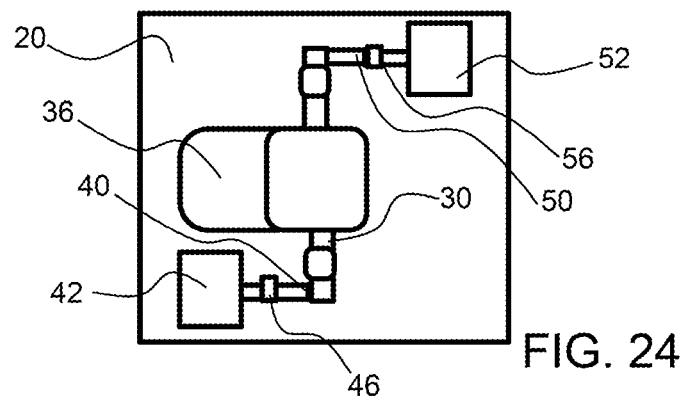
FIG. 24 shows a diagram of the perturbation portion of a muscle memory training apparatus shown in FIG. 23, with the first arm weight and second arm weight changed to heavier arm weights to increase the amount of force created by the perturbation portion.

As shown in FIG. 24, a perturbation portion 21 of a muscle memory training apparatus 10 has the first arm 40 configured in a substantially opposing rotational position as the second arm 50 as shown in FIG. 23. However, the first arm weight 42 and second arm weight 52 have been changed from those shown in FIG. 23 to heavier arm weights to increase the amount of force created by the perturbation portion. The heavier weights are represented as larger in FIG. 24 to those shown in FIG. 23, however the weight may be changed but the size of the arm weight may stay substantially the same.

Figure 25:
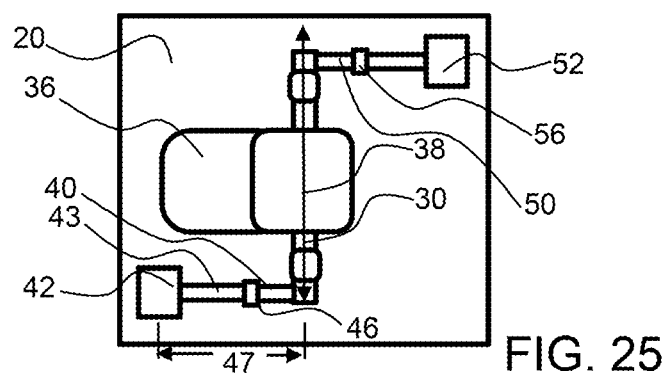
FIG. 25 shows a diagram of the perturbation portion of a muscle memory training apparatus shown in FIG. 23, with the first arm weight and second arm weight extended further from the axle to produce more force.

As shown in FIG. 25, a perturbation portion 21 of a muscle memory training apparatus 10 has the first arm 40 configured in a substantially opposing rotational position as the second arm 50 or about 180 degrees, as shown in FIG. 23. However, the first arm weight 42 and second arm weight 52 are configured a greater offset distance from the axle than the first arm weight and second arm weights shown in FIG. 23. The first arm weight arm 43 and second arm weight arm 53 may be changed or extended out further from the first arm weight coupler 46 and second arm weight coupler 56 to produce said greater offset distance. The torque offset distance 47, the distance from the rotational axis 38 of the axle 30 and the center of mass of the first arm weight 42 is shown in FIGS. 23 and 25, wherein this torque offset distance is greater in FIG. 25.

FIGS. 26, 27, 28 and 29 are referenced and described to explain why the apparatus and user tremor frequency must be the same within a narrow margin and how tremor frequency is measured.

The frequency of the perturbation is synchronized with the user's natural reflex loop time. In this manner, the frequencies will entrain; their phase relationship will align, and they will summate correctly. The resultant perturbation force applied to the user is the sum of the muscle contraction force produced by the reflex plus the perturbation force produced by the perturbator. In effect, the reflex force is increased by the perturbation force, or the reflex muscle contraction force is amplified by the addition of the perturbator force. The frequency of the muscle memory training apparatus must be substantially the same as (within about 25%) of a tremor frequency, or frequency of involuntary movements, such as about 2 Hz or more, about 4 Hz or more, about 6 Hz or more, about 8 Hz or more, about 10 Hz or more and any range between and including the frequencies provided such as from about 2 Hz to 10 Hz. A perturbation frequency of the muscle memory training may be a frequency of revolution of the arms such as revolutions per minute which would be 60 rpm for 1 Hz, or it may be half of the tremor frequency, or 30 rpm for a 1 Hz tremor frequency, as the arms may create alternating perturbation forces within one revolution. People with Parkinson's disease have tremors with a frequency of about 4 Hz to 6 Hz, and people with essential tremor may have a frequency of about 5 Hz to 8 Hz and therefore a range of about 4 Hz to 8 Hz may cover the range of frequencies for tremors. If the frequencies are not substantially the same, they will not entrain, summate correctly, and produce a resultant force that is irregular and not a replica of the tremor frequency.

For example, if the frequency is greater than the reflex loop time [time from stimulation to completion of muscle contraction]. A tetanic muscle contraction occurs. When repeated stimuli occur at short intervals the muscle doesn't have time to fully relax before it is called upon to contract again. Movement becomes erratic, ceases, or becomes rigid.

As shown in FIG. 26, in the first frame or time period (1), a single perturbation effectuates a single reflex. In the second frame, or time period (2), a second perturbation occurs before the first reflex is completed. In the third frame or time period (3), multiple perturbations occur before any reflex is completed. The effect is cumulative. In the fourth frame (4), full tetanus occurs and there is no muscle relaxation between perturbations. A line showing the perturbations 8 as a function of time is shown in the third frame. A line representing a reflex 9 is shown as a function of time above the perturbation line. The frequency of perturbation 8 In the fourth frame (4) are too fast for the reflex 9 to respond and results in a tectonic state.

Starting a reflex movement before the prior movement is completed is like practicing a golf swing wherein successive swings are started before the current swing is completed. When perturbation and reflex movements of the same frequency are added together, the resultant movement will be the same frequency, maximum amplitude, and consistent. FIG. 27 shows the desired effect wherein the frequencies and phase are the same. The resultant movement A+B is the sum of both movements A and B.

However, when the movement frequencies differ, the resultant movement will be a complex summation of forces that undergo constant change. FIG. 28 shows the summation of 2 frequencies, one of which is twice the other. The phase and amplitude relationships do not summate correctly for this application. Every combination of 2 forces occurring at different frequencies or phase relationships, yields a complex movement.

Perturbation frequency is an important setting. The intent is to practice the reflex movement, not some derivative movement that can do more harm than good.

Fatigue

Reflexes occurring at a high frequency over a protracted period can lead to synaptic, muscle, and other forms of fatigue that cause short or long-term deficit performance. Reflexes begin to fail. Stability is inadequate and may even contribute to instability. Practice challenges fatigue and can improve strength and endurance. Not unlike building muscles, subject them to heightened demands and make them bigger, stronger, and less susceptible to fatigue.

Figure 29:
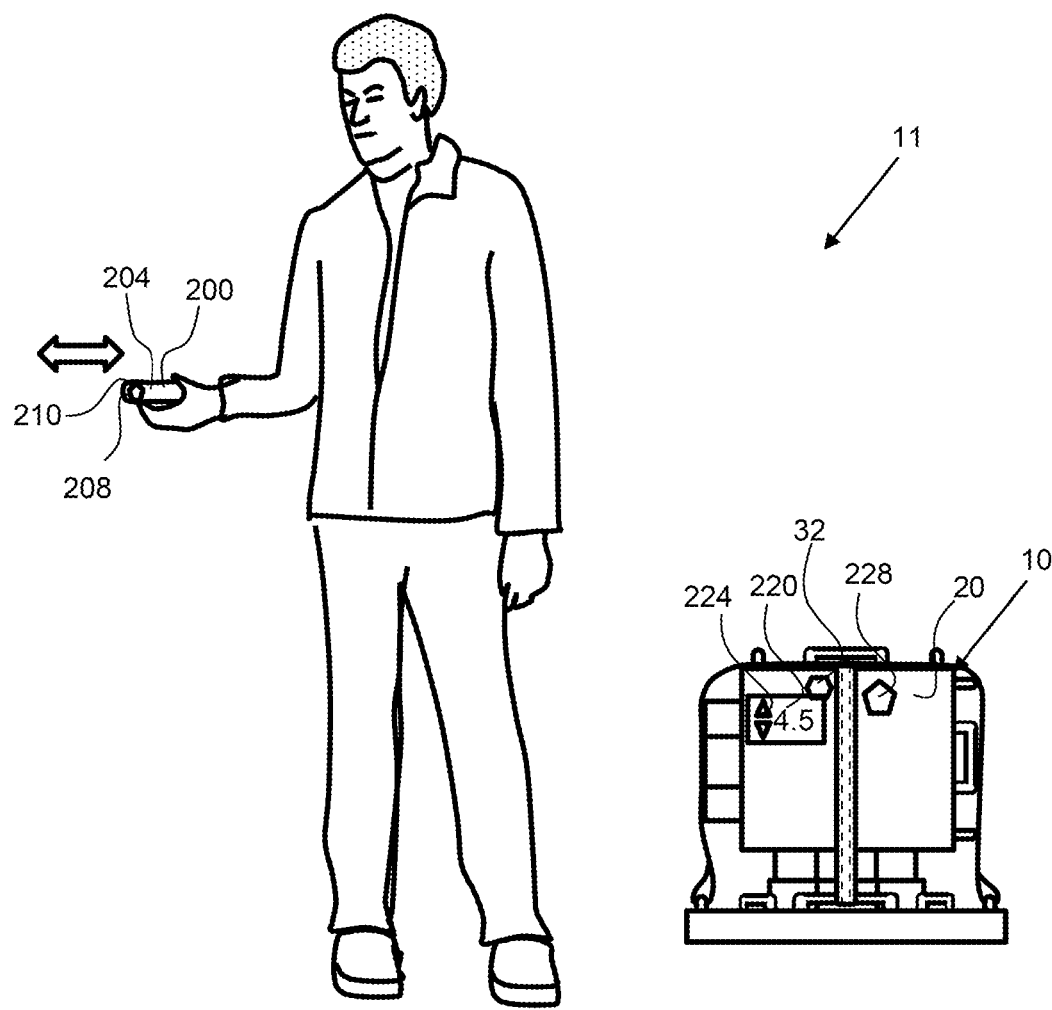
FIG. 29 shows a muscle memory training system having a muscle memory training apparatus that is configured to operate at a frequency that is measured by a tremor frequency device.

As shown in FIG. 29, a muscle memory training system 11 includes a muscle memory training apparatus 10 that is configured to operate at a frequency measured by a tremor frequency device 200. A person is holding the tremor frequency device 200 that includes a gyroscope 204 that measures the frequency of the tremor or involuntary movement of the person. The tremor frequency device 200 may be a mobile device, such as a mobile phone. The tremor frequency device 200 may have a wireless transmitter 208 that transmits the measured frequency to the muscle memory training apparatus 10. The muscle memory training apparatus 10 may have a wireless signal receiver 228 that receives the wireless signal from the tremor frequency device 200 with the measured tremor frequency. A controller 32 of the muscle memory training apparatus 10 may then automatically set the perturbation frequency of the muscle memory training apparatus 10 to match this measured tremor frequency. The controller 32 may be located on the housing 20 or may be coupled wirelessly with the motor or have a wired connection with the motor. The frequency of the muscle memory training apparatus 10 may be the revolutions per minute of an arm. Also, the muscle memory training apparatus 10 may have a frequency display and a frequency input 224 to enable a user to manually input or adjust the measured tremor frequency or a desired perturbation frequency of the muscle memory training apparatus 10. A perturbating force may be set automatically or manually to a perturbation frequency that is substantially the same (within 25%) as a tremor frequency.

In summary, the apparatus is designed to deliver programmed perturbations to stabilization reflexes whilst the user is engaged in daily living or planned activities. A muscle memories training system is designed and configured to retrain reflex stabilization and voluntary muscle memories for a person with a movement disorder such as Parkinson's or essential tremor. A movement disorder includes but is not limited to Parkinson's, essential tremor, ataxia, dystonia, Huntington's disease, and Tardive Dyskinesia.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A muscle memory training system to retrain reflex stabilization and voluntary muscle memories for a person with a movement disorder comprising:
   a) a reflex muscle memory training apparatus comprising:
      i) a housing comprising a motor with an axle;
      ii) a first arm extending from the axle;
      iii) a first arm weight coupled to the first arm;
      iv) a means to detachably attach the housing to a person;

wherein the motor is configured to spin the first arm weight about the axle about a rotational axis to produce a perturbating force at a perturbation frequency that is substantially the same as a tremor frequency of a person with a tremor to synchronize the perturbating force with said tremor to amplify a resulting movement and retrain said reflex stabilization muscle memories by practicing said reflex stabilization muscle memories to the perturbating force; and wherein the muscle memory training system is configured for a person to practice voluntary movements concurrently with the perturbations to retrain them to function on a stabilized platform;

wherein the first arm weight has a torque offset distance from a rotational axis of the axle and wherein the torque offset distance is adjustable; and wherein the first arm weight is coupled to a first arm weight arm and wherein the first arm weight arm is configured to be interchanged with a longer first arm weight arm having a length greater by at least 20% than a length of the first arm weight arm.

2. The muscle memory training system of claim 1, wherein the perturbation frequency is between 2 Hz and 10 Hz.

3. The muscle memory training system of claim 1, wherein the perturbation frequency is between 2 Hz and 8 Hz.

4. The muscle memory training system of claim 1, further comprising a tremor frequency measuring device configured to measure tremor frequency of said person having a tremor.

5. The muscle memory training system of claim 4, wherein the muscle memory training system is configured to set the perturbation frequency to the measured tremor frequency to synchronize the perturbating force with the tremor to amplify a resulting movement.

6. The muscle memory training system of claim 5, wherein the perturbating force is at a perturbation frequency that is between 2 Hz and 10 Hz.

7. The muscle memory training system of claim 6, wherein the tremor frequency measuring device is separate from the housing.

8. The muscle memory training system of claim 7, wherein the tremor frequency measuring device has a wireless transmitter, and wherein the muscle memory training apparatus further comprises a wireless signal receiver configured to receive a measured tremor frequency from a wireless signal from the tremor frequency measuring device.

9. The muscle memory training system of claim 8, wherein the muscle memory training apparatus further comprises a controller and wherein the controller is configured to set a perturbation frequency to the measured tremor frequency.

10. The muscle memory training system of claim 6, wherein the tremor frequency measuring device a hand-held device.

11. The muscle memory training system of claim 6, wherein the tremor frequency measuring device is a mobile phone.

12. A method of retraining reflex stabilization muscle memories comprising:
    a) providing the muscle memory training system of claim 1;
    b) spinning the first arm and first arm weight to produce a perturbating force on said person; and
    c) performing a voluntary movement;

wherein the person involuntarily reacts to counter the perturbating force while performing said voluntary movement concurrently and thereby retraining their reflex stabilization muscle memories.

13. The method of claim 12, wherein the perturbating force is at a perturbation frequency that is between 2 Hz and 10 Hz.

14. The method of claim 12, wherein the perturbating force is at a perturbation frequency that is between 2 Hz and 8 Hz.

15. The method of claim 12, further comprising a tremor frequency measuring device to measure a measured tremor frequency of said person.

16. The method of claim 15, wherein the perturbation frequency is set to the measured tremor frequency.

17. The method of claim 16, wherein the tremor frequency device is separate from the housing.

18. The method of claim 17, wherein the tremor frequency device has a wireless transmitter, and wherein the muscle memory training apparatus further comprises a wireless signal receiver configured to receive a measured tremor frequency from a wireless signal from the tremor frequency device.

19. The method of claim 18, wherein the muscle memory training apparatus further comprises a controller and wherein the controller sets a perturbation frequency to the measured tremor frequency.

20. The method of claim 16, wherein the tremor frequency device is a mobile phone.

* * * * *